(12) United States Patent
Uribe et al.

(10) Patent No.: US 7,723,690 B2
(45) Date of Patent: May 25, 2010

(54) ADJUSTABLE SLIT COLLIMATORS METHOD AND SYSTEM

(75) Inventors: Jorge Uribe, Niskayuna, NY (US); James William Hugg, Glenville, NY (US); Floribertus P. M. Heukensfeldt Jansen, Ballston Lake, NY (US)

(73) Assignee: General Electric Company, Niskayuna, NY (US)

(*) Notice: Subject to any disclaimer, the term of this patent is extended or adjusted under 35 U.S.C. 154(b) by 380 days.

(21) Appl. No.: 11/731,873

(22) Filed: Mar. 30, 2007

(65) Prior Publication Data

US 2008/0237473 A1   Oct. 2, 2008

(51) Int. Cl.
*G01T 1/166* (2006.01)
*G01T 1/16* (2006.01)

(52) U.S. Cl. .............. 250/363.1; 250/363.02; 250/363.04; 378/147; 378/148; 378/149

(58) Field of Classification Search .............. 250/363.1; 378/147–153
See application file for complete search history.

(56) References Cited

U.S. PATENT DOCUMENTS

| | | | |
|---|---|---|---|
| 4,289,965 A | 9/1981 | Koga |
| 4,389,569 A | 6/1983 | Hattori |
| 5,032,728 A | 7/1991 | Chang |
| 5,825,031 A | 10/1998 | Wong |
| 6,504,157 B2 | 1/2003 | Juhi |
| 6,525,320 B1 | 2/2003 | Juni |
| 6,525,321 B2 | 2/2003 | Juni |
| D474,277 S | 5/2003 | Juni |

(Continued)

FOREIGN PATENT DOCUMENTS

WO   WO 2005/006977   1/2005

(Continued)

OTHER PUBLICATIONS

M Freed, MA Kupinski, LR Furenlid, MK Whitaker, and HH Barrett, Innovative Imaging II—A prototype instrument for adaptive SPECT imaging, SPIE Conference: Physics of Medical Imaging, Session 6, Feb. 2007.

(Continued)

*Primary Examiner*—David P Porta
*Assistant Examiner*—Casey Bryant
(74) *Attorney, Agent, or Firm*—Scott J. Asmus

(57) ABSTRACT

Embodiments relate to a slit collimator assembly including a first set of panels spaced at least partially around a longitudinal axis of the collimator assembly and extending generally parallel to the longitudinal axis. The slit collimator assembly further includes a second set of panels spaced at least partially around longitudinal axis of the collimator assembly and extending generally parallel to the longitudinal axis. The first set of panels and the second set of panels are arranged to define one or more slit apertures. The slit collimator assembly is configured so that movement of at least one of the first set of panels or the second set of panels adjusts an aperture size of at least one of the one or more slit apertures. The slit collimator assembly is configured so that gamma rays can pass through the one or more slit apertures, but the remainder of the collimator assembly is substantially gamma ray absorbent. Embodiments also relate to imaging systems and methods of changing collimator performance.

21 Claims, 18 Drawing Sheets

U.S. PATENT DOCUMENTS

| | | |
|---|---|---|
| D492,998 S | 7/2004 | Juni |
| 7,012,257 B2 | 3/2006 | Juni |
| 7,015,476 B2 | 3/2006 | Juni |
| 7,023,962 B2 * | 4/2006 | Xu et al. ............ 378/147 |
| 7,071,473 B2 | 7/2006 | Juni |
| 7,105,825 B2 | 9/2006 | Juni |
| 7,138,638 B2 | 11/2006 | Juni |
| 7,439,514 B1 | 10/2008 | Uribe |
| 2004/0239941 A1 | 12/2004 | Schramm |
| 2006/0050845 A1 | 3/2006 | Juni |
| 2006/0192308 A1 | 8/2006 | Juni |
| 2007/0007455 A1 | 1/2007 | Juni |
| 2008/0237472 A1 | 10/2008 | Uribe et al. |
| 2008/0304619 A1 | 12/2008 | Uribe et al. |
| 2009/0022278 A1 | 1/2009 | Uribe et al. |

FOREIGN PATENT DOCUMENTS

WO  WO 2006/029163  3/2006

OTHER PUBLICATIONS

M Freed, MA Kupinski, LR Furenlid, JY Hesterman, E Clarkson and HH Barrett, Adaptive Imaging, "Design of an Adaptive SPECT Imager", Academy of Molecular Imaging Annual Conference, Mar. 2006 and "Adaptive imaging techniques for nuclear medicine", Society of Nuclear Medicine, Annual Meeting, 2006.

HH Barrett, LR Furenlid, ME Freed, JY Hesterman, MA Kupinski and EW Clarkson, Theory of Adaptive SPECT Imaging, IEEE Medical Imaging Conference, Session M13: SPECT and SPECT/CT Nov. 2006.

* cited by examiner

ADJUSTABLE SLIT COLLIMATORS METHOD AND SYSTEM

BACKGROUND

The invention relates generally to non-invasive imaging such as single photon emission computed tomography (SPECT) imaging. More particularly, the invention relates to adjustable collimators for use in non-invasive imaging.

SPECT is used for a wide variety of imaging applications, such as medical imaging. In general, SPECT systems are imaging systems that are configured to generate an image based upon the impact of photons (generated by a nuclear decay event) against a gamma-ray detector. In medical and research contexts, these detected photons may be processed to formulate an image of organs or tissues beneath the skin.

To produce an image, one or more detector assemblies may be rotated around a subject. Detector assemblies are typically comprised of various structures working together to receive and process the incoming photons. For instance, the detector assembly may utilize a scintillator assembly (e.g., large sodium iodide scintillator plates) to convert the photons into visible light for detection by an optical sensor. This scintillator assembly may be coupled by a light guide to multiple photomultiplier tubes (PMTs) or other light sensors that convert the light from the scintillator assembly into an electric signal. In addition to the scintillator assembly-PMT combination, pixilated solid-state direct conversion detectors (e.g., CZT) may also be used to generate electric signals from the impact of the photons. This electric signal can be transferred, converted, and processed by electronic modules in a data acquisition module to facilitate viewing and manipulation by clinicians.

Typically, SPECT systems further include a collimator assembly that may be attached to the front of the gamma-ray detector. In general, the collimator assembly is designed to absorb photons such that only photons traveling in certain directions impact the detector assembly. The collimator assembly selected for use with the SPECT system impacts the system performance thereof, including image resolution and sensitivity. Because resolution and sensitivity may be traded off along a collimator performance curve for each SPECT system, a single operating point typically may be selected when designing a collimator assembly. In other words, a collimator assembly is typically designed to operate at a single operating point on the resolution-sensitivity tradeoff performance curve. Different applications, however, may benefit from operating with different tradeoffs on the performance curve. By way of example, small organ imaging typically may require higher resolution and lower sensitivity, whereas imaging a large volume (such as for possible lesions) typically may require higher sensitivity with lower resolution.

To provide a SPECT system with different tradeoffs on the performance curve, multiple collimator assemblies may be provided for each SPECT system with each of the collimator assemblies having a different performance point. In this manner, a user may have a choice in selecting a collimator assembly with an appropriate operating point for a particular application. Accordingly, when the user changes applications, the most appropriate collimator assembly must be mounted on the SPECT system. Collimator assemblies, however, are typically heavy, generally comprising lead with a thickness sufficient to block gamma rays so that the collimator exchange is a time consuming process. To minimize this time-consuming exchange, extra effort may be made to schedule blocks of patients with similar examination requirements, for example, in clinical laboratories. In addition to the problems associate with the time-consuming exchange of the collimator assemblies, the purchase and storage of multiple collimator assemblies is costly.

Accordingly, it would be desirable to provide an imaging system with collimator assemblies having different operating points along the resolution-sensitivity tradeoff performance curve while reducing the need for multiple collimator assemblies.

BRIEF DESCRIPTION

In accordance with another embodiment, the present technique provides a slit collimator assembly including a first set of panels spaced at least partially around a longitudinal axis of the collimator assembly and extending generally parallel to the longitudinal axis. The slit collimator assembly further includes a second set of panels spaced at least partially around a longitudinal axis of the collimator assembly and extending generally parallel to the longitudinal axis. The first set of panels and the second set of panels are arranged to define one or more slit apertures. The collimator assembly is configured so that movement of at least one of the first set of panels or the second set of panels adjusts an aperture size of at least one of the one or more slit apertures. The collimator assembly is configured so that gamma rays can pass through the one or more slit apertures, but the remainder of the collimator assembly is substantially gamma ray absorbent.

In accordance with another embodiment, the present technique provides an imaging system. The imaging system includes a slit collimator assembly and a detector assembly. The slit collimator assembly includes a first set of panels spaced at least partially around a longitudinal axis of the collimator assembly and extending generally parallel to the longitudinal axis. The slit collimator assembly further includes a second set of panels spaced at least partially around a longitudinal axis of the collimator assembly and extending generally parallel to the longitudinal axis. The first set of panels and the second set of panels are arranged to define one or more slit apertures. The collimator assembly is configured so that movement of at least one of the first set of panels or the second set of panels adjusts an aperture size of at least one of the one or more slit apertures. The detector assembly is configured to detect and generate one or more signals in response to gamma rays that pass through the one or more slit apertures in the collimator assembly.

In accordance with another embodiment, the present technique provides a method of adjusting slit collimator performance. The method includes moving at least one of a first set of panels of the collimator assembly or a second set of panels of the collimator assembly to adjust an aperture size of one or more slit apertures defined by the first set of panels and the second set of panels. The first set of panels are spaced at least partially around a longitudinal axis of the collimator assembly and extend generally parallel to the longitudinal axis. The second set of panels are spaced at least partially around the longitudinal axis of the collimator assembly and extend generally parallel to the longitudinal axis. The method further includes collimating gamma rays with the collimator assembly. The method further includes detecting the collimated gamma rays.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

I. Exemplary SPECT System

Figure 1:
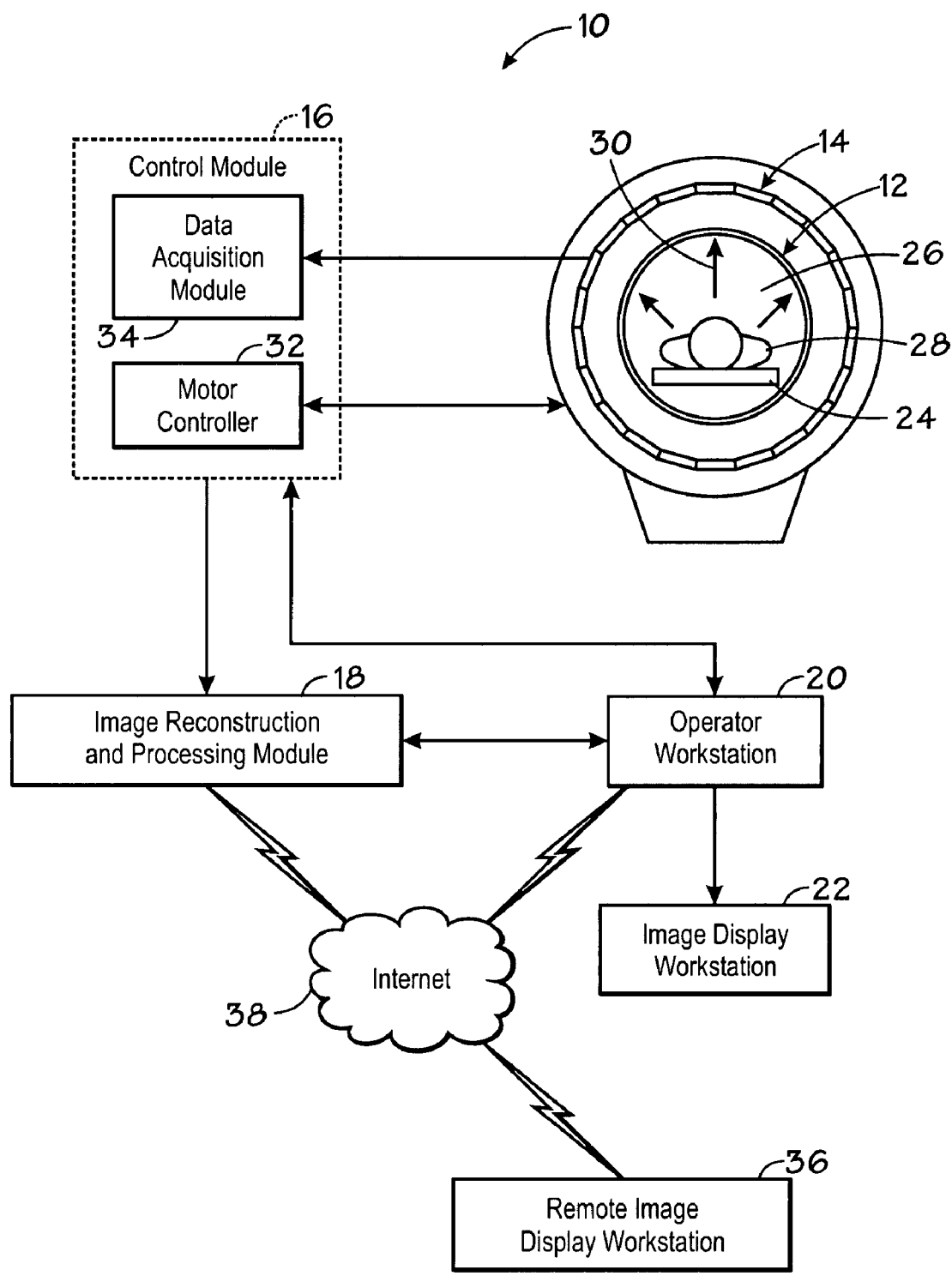
FIG. 1 is an illustration of an exemplary SPECT system which may include a collimator assembly in accordance with embodiments of the present technique.

FIG. 1 illustrates an exemplary SPECT system 10 for acquiring and processing image data in accordance with exemplary embodiments of the present technique. In the illustrated embodiment, SPECT system 10 includes a collimator assembly 12 and a detector assembly 14. The SPECT system 10 also includes a control module 16, an image reconstruction and processing module 18, an operator workstation 20, and an image display workstation 22. Each of the aforementioned components will be discussed in greater detail in the sections that follow.

As illustrated, a subject support 24 (e.g. a table) may be moved into position in a field of view 26 of the SPECT system 10. In the illustrated embodiment, the subject support 24 is configured to support a subject 28 (e.g., a human patient, a small animal, a plant, a porous object, etc.) in a position for scanning. Alternatively, the subject support 24 may be stationary, while the SPECT system 10 may be moved into position around the subject 28 for scanning. Those of ordinary skill in the art will appreciate that the subject 28 may be supported in any suitable position for scanning. By way of example, the subject 28 may be supported in the field of view 26 in a generally vertical position, a generally horizontal position, or any other suitable position (e.g., inclined) for the desired scan. In SPECT imaging, the subject 28 is typically injected with a solution that contains a radioactive tracer. The solution is distributed and absorbed throughout the subject 28 in different degrees, depending on the tracer employed and, in the case of living subjects, the functioning of the organs and tissues. The radioactive tracer emits electromagnetic rays 30 (e.g., photons or gamma quanta) known as "gamma rays" during a nuclear decay event.

As previously mentioned, the SPECT system 10 includes the collimator assembly 12 that receives the gamma rays 30 emanating from the subject 28 positioned in the field of view 26. As will be described below, the collimator assembly 12 is generally configured to limit and define the direction and angular divergence of the gamma rays 30. In general, the collimator assembly 12 is disposed between the detector assembly 14 and the field of view 26. As will be discussed in more detail with respect to the following figures, the collimator assembly 12 may include one or more of a slit aperture collimator, a pinhole aperture collimator, or a combination thereof. Accordingly, the collimator assembly generally contains slit apertures, pinholes apertures, or both therethrough. In accordance with exemplary embodiments of the present technique, one or more of the pinhole apertures and the slits apertures have an aperture size that is adjustable. Those of ordinary skill in the art will appreciate that through adjustment of the aperture size the performance of the collimator assembly 12 may be changed and thus the resolution and sensitivity of the SPECT system 10 may also be changed. Moreover, the collimator assembly 12 may contain a radiation-absorbent material, such as lead or tungsten, for example. Referring again to FIG. 1, the collimator assembly 12 extends at least partially around the field of view 26. In exemplary embodiments, the collimator assembly 12 may extend up to about 360° around the field of view 26. By way of example, the collimator assembly 12 may extend from about 180° to about 360° around the field of view 26.

The gamma rays 30 that pass through the collimator assembly 12 impact the detector assembly 14. Due to the collimation of the gamma rays 30 by the collimator assembly 12, the detection of the gamma rays 30 may be used to determine the line of response along which each of the gamma rays 30 traveled before impacting the detector assembly 14, allowing localization of each gamma ray's origin to that line. In general, the detector assembly 14 may includes a plurality of detector elements configured to detect the gamma rays 30 emanating from the subject 28 in the field of view 26 and passing through one or more apertures defined by the collimator assembly 12. In exemplary embodiments, each of the plurality of detector elements in the detector assembly 14 produces an electrical signal in response to the impact of the gamma rays 30.

As will be appreciated by those of ordinary skill in the art, the detector elements of the detector assembly 14 may include any of a variety of suitable materials and/or circuits for detecting the impact of the gamma rays 30. By way of example, the detector elements may include a plurality of solid-state detector elements, which may be provided as one-dimensional or two-dimensional arrays. In another embodiment, the detector elements of the detector assembly 14 may include a scintillation assembly and PMTs or other light sensors.

Moreover, the detector elements may be arranged in the detector assembly 14 in any suitable manner. By way of example, the detector assembly 14 may extend at least partially around the field of view 26. In certain embodiments, the detector assembly 14 may include modular detector elements arranged around the field of view 26. Alternatively, the detector assembly 14 may be arranged in a ring that may extend up to about 360° around the field of view 26. In certain exemplary embodiments, the detector assembly 14 may extend from about 180° to about 360° around the field of view 26. The ring of detector elements may include flat panels or curved detector surfaces (e.g., a NaI annulus). In one exemplary embodiment, the ring may comprise in the range from 9-10 solid-state detector panels with each detector panel comprising four detector modules. Those of ordinary skill in the art will appreciate that the ring need not be circular, for example, the detector elements may be arranged in an elliptical ring or be contoured to the body profile of the subject 28. In addition, in certain exemplary embodiments, the detector assembly 14 may be gimbaled on its support base, e.g., so that arbitrary slice angles may be acquired.

To acquire multiple lines of response emanating from the subject 28 in the field of view 26 during a scan, the collimator assembly 12 may be configured to rotate about the subject 28 positioned within the field of view 26. In accordance with exemplary embodiments, the collimator assembly 12 may be configured to rotate with respect to the detector assembly 14. By way of example, the detector assembly 14 may be stationary while the collimator assembly 12 may be configured to rotate about the field of view 26. Alternatively, the detector assembly 14 may rotate while the collimator assembly 12 is stationary. In certain exemplary embodiments, the collimator assembly 12 and the detector assembly 14 may both be configured to rotate, either together or independent of one another. Alternatively, if sufficient pinhole apertures and/or slit apertures are provided through the collimator assembly 12, then no rotation may be required. Also, if the slit apertures are orthogonal to the longitudinal axis of the collimator assembly 12 then no rotation may be required. Such exemplary embodiment could include axial displacement of the collimator assembly 12 relative to the detector assembly 14. By way of example, the detector assembly 14 may be stationary while the collimator assembly 12 may be configured to slide along its axial direction. Alternatively, the detector assembly 14 may slide along its axial direction while the collimator assembly 12 is stationary, for example. In certain exemplary embodiments, the collimator assembly 12 and the detector assembly 14 may both be configured to slide, either together or independent of one another.

SPECT system 10 further includes a control module 16. In the illustrated embodiment, the control module 16 includes a motor controller 32 and a data acquisition module 34. In general, the motor controller 32 may control the rotational and/or longitudinal speed and position of the collimator assembly 12, the detector assembly 14, and/or the position of the subject support 24. The data acquisition module 34 may be configured to obtain the signals generated in response to the impact of the gamma rays 30 with the detector assembly 14. For example, the data acquisition module 34 may receive sampled electrical signals from the detector assembly 14 and convert the data to digital signals for subsequent processing by the image reconstruction and processing module 18.

Those of ordinary skill in the art will appreciate that any suitable technique for data acquisition may be used with the SPECT system 10. By way of example, the data needed for image reconstruction may be acquired in a list or a frame mode.

In one exemplary embodiment of the present technique, gamma ray events (e.g., the impact of gamma rays 30 on the detector assembly 14), gantry motion (e.g., collimator assembly 12 motion and subject support 24 position), and physiological signals (e.g., heart beat and respiration) may be acquired in a list mode. For example, a time-stamp may be associated with each gamma ray event (e.g., energy and position) or by interspersing regular time stamps (e.g., every 1 ms) into the list of gamma ray events. The physiological signals may be included in the list, for example, when they change by a defined amount or with every regular time stamp. In addition, gantry motion may also be included in the event lists, for example, when it changes by a defined amount or with every regular time stamp. The list mode data may be binned by time, gantry motion or physiological gates before reconstruction. List mode may be suitable in exemplary embodiments where the count rate is relatively low and many pixels record no counts at each gantry position or physiological gate.

Alternatively, frames and physiological gates may be acquired by moving the gantry in a step-and-shoot manner and storing the number of events in each pixel during each frame time and heart or respiration cycle phase. Frame mode may be suitable, for example, where the count rate is relatively high and most pixels are recording counts at each gantry position or physiological gate.

In the illustrated embodiment, the image reconstruction and processing module 18 is coupled to the data acquisition module 34. The signals acquired by the data acquisition module 34 are provided to the image reconstruction and processing module 18 for image reconstruction. The image reconstruction and processing module 18 may include electronic circuitry to receive acquired signals and electronic circuitry to condition the acquired signals. Further, the image reconstruction and processing module 18 may include processing to coordinate functions of the SPECT system 10 and implement reconstruction algorithms suitable for reconstruction of the acquired signals. The image reconstruction and processing module 18 may include a digital signal processor, memory, a central processing unit (CPU) or the like, for processing the acquired signals. As will be appreciated, the processing may include the use of one or more computers. The addition of a separate CPU may provide additional functions for image reconstruction, including, but not limited to, signal processing of data received, and transmission of data to the operator workstation 20 and image display workstation 22. In one embodiment, the CPU may be confined within the image reconstruction and processing module 34, while in another embodiment a CPU may include a stand-alone device that is separate from the image reconstruction and processing module 34.

The reconstructed image may be provided to the operator workstation 20. The operator workstation 20 may be utilized by a system operator to provide control instructions to some or all of the described components and for configuring the various operating parameters that aid in data acquisition and image generation. An image display workstation 22 coupled to the operator workstation 20 may be utilized to observe the reconstructed image. It should be further noted that the operator workstation 20 and the image display workstation 22 may be coupled to other output devices, which may include printers and standard or special purpose computer monitors. In general, displays, printers, workstations, and similar devices supplied with the SPECT system 10 may be local to the data acquisition components, or may be remote from these components, such as elsewhere within the institution or hospital, or in an entirely different location, linked to the image acquisition system via one or more configurable networks, such as the Internet, virtual private networks, and so forth. By way of example, the operator workstation 20 and/or the image reconstruction and processing module 18 may be coupled to a remote image display workstation 36 via a network (represented on FIG. 1 as Internet 38).

Furthermore, those of ordinary skill in the art will appreciate that any suitable technique for image reconstruction may be used with the SPECT system 10. In one exemplary embodiment, iterative reconstruction (e.g., ordered subsets expectation maximization, OSEM) may be used. Iterative reconstruction may be suitable for certain implementations of the SPECT system 10 due, for example, to its speed and the ability to tradeoff reconstruction resolution and noise by varying the convergence and number of iterations.

While in the illustrated embodiment, the control module 16 (including the data acquisition module 34 and the motor controller 32) and the image reconstruction and processing module 18 are shown as being outside the detector assembly 14 and the operator workstation 20. In certain other implementations, some or all of these components may be provided as part of the detector assembly 14, the operator workstation 20, and/or other components of the SPECT system 10.

Those of ordinary skill in the art will appreciate that the performance of the SPECT system 10 is at least partially based on the collimator assembly selected for use therewith. By way of example, system resolution and sensitivity may be traded off along a collimator performance curve for the SPECT system 10. Different configuration of collimator and detector assemblies could have different performance curves, for example. In some instances, a collimator assembly may be designed to operate at only a single operating point on the resolution-sensitivity tradeoff curve. Different applications, however, may benefit from operating with different tradeoffs on the performance curve. To provide different resolutions and sensitivities, multiple swappable collimator assemblies may be provided for each SPECT system with each collimator assembly having a different performance point. However, this may add undesired expense and complexity associated with obtaining, storing and swapping the collimator assemblies.

An embodiment of the present technique provides a collimator assembly 12 that reduces the need for multiple collimator assemblies. In accordance with embodiments of the present technique, the collimator assembly 12 has one or more adjustable apertures therein. In general, the one or more adjustable apertures in the collimator assembly 12 have an aperture size that is adjustable. The adjustable apertures in the collimator assembly 12 may include pinhole apertures, slit apertures, or a combination thereof. By adjustment of the aperture size of the one or more adjustable apertures in the collimator assembly 12, the resolution and/or sensitivity of the SPECT system 10 may be changed without the need for additional collimator assemblies.

Moreover, the collimator assembly 12 may be configured to allow adjustment of the aperture size during an examination. This may be desirable, for example, so that multiple scans of the subject 28 may be performed with different resolutions and sensitivities. In certain embodiments, aperture size may be adjusted during the examination without the need for removal of the subject 28 from the SPECT system 10. Accordingly, the collimator assembly 12 may be configured to allow for aperture adjustment without removal of the subject 28 from the SPECT system 10. In one embodiment, the aperture adjustment may be automated. The capability to adjust collimator performance during an examination enables adaptive SPECT methods, wherein performance of the SPECT system can be adapted in an optimal way to the specific imaging task and specific subject. By way of example, a first image (e.g., a "scout image") may be acquired in a configuration of higher sensitivity and lower resolution. In certain exemplary embodiments, the first image may be of a heart. Then, depending on the specific subject position, size, shape and distribution of gamma-ray attenuating tissues, the collimator configuration may be adjusted, for example, to provide optimum sensitivity and resolution for the imaging task, such as identification of myocardial infarcation or the measurement of myocardial perfusion or ventricular ejection fraction. A second image may then be obtained during the same examination without removal of the subject 28. Based on the optimum sensitivity and resolution, this second image may be at a higher resolution but lower sensitivity than the first image. In another example, a first image may be obtained with a short acquisition time to adjust the positioning and focusing of the imaging system 10 on the particular organ/part of the subject 28. Then, a second image of higher quality may be acquired, often at a longer duration. In this manner, the imaging system 10 can be optimized for each subject based on the requirements of the desired imaging task.

II. Exemplary Pinhole Aperture Collimator Embodiments

Figure 2:
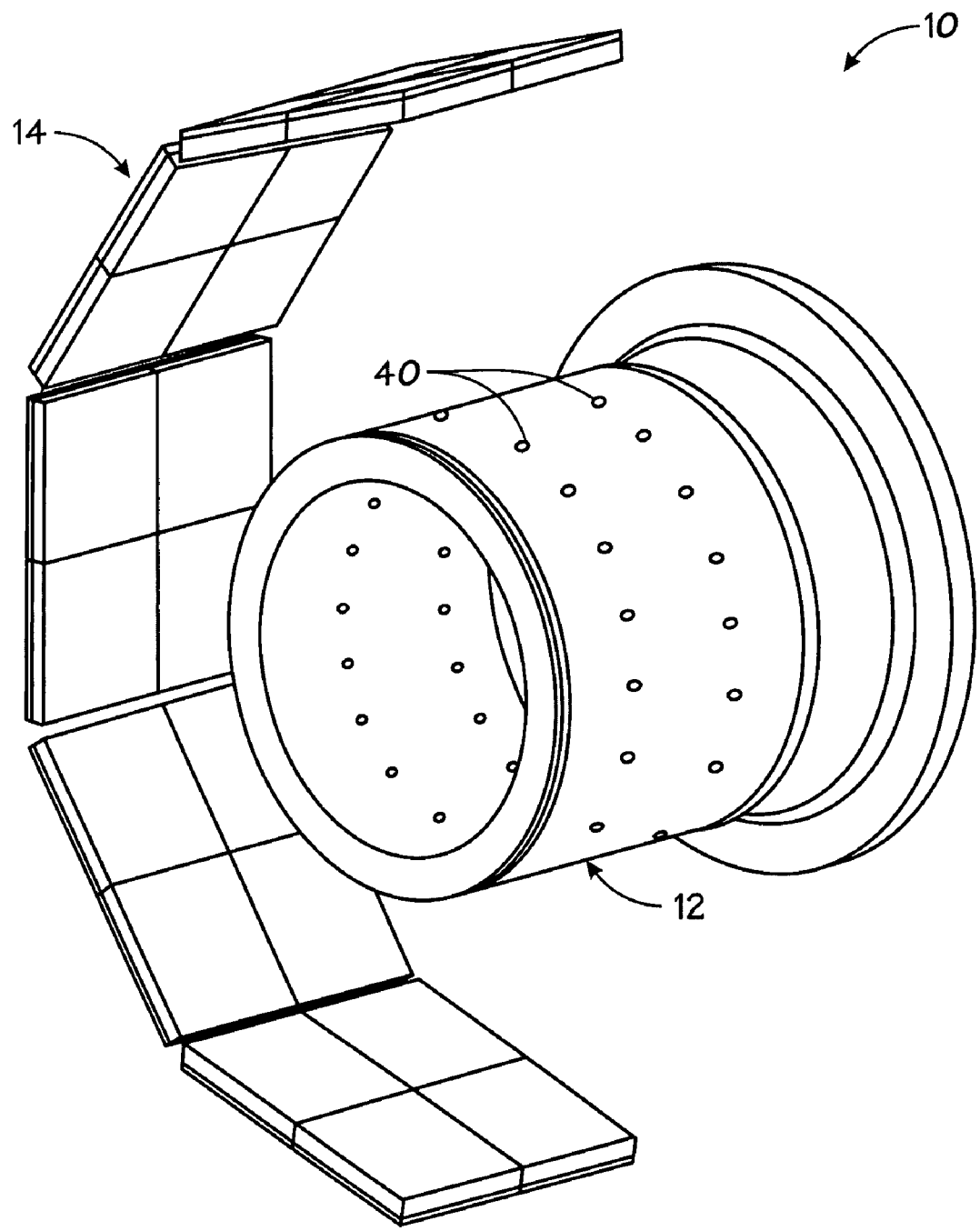
FIG. 2 is a perspective view of an exemplary SPECT system that includes a pinhole aperture collimator in accordance with embodiments of the present technique.

Referring now to FIG. 2, an exemplary collimator assembly 12 having one or more adjustable pinhole apertures 40 is illustrated, in accordance with embodiments of the present technique. In the illustrated embodiment, a detector assembly 14 encircles the collimator assembly 12. As illustrated, a portion of the detector assembly 14 is removed to illustrate the components of the collimator assembly 12, particularly the one or more pinhole apertures 40.

In general, gamma rays aligned with the pinhole apertures 40 should pass through the collimator assembly 12, while gamma rays that are not aligned with the pinhole apertures 40 should be absorbed by the collimator assembly 12. In the illustrated embodiment, the pinhole apertures 40 in the collimator assembly 12 are arranged in two staggered rows. The pinhole apertures 40, however, may be arranged in the collimator assembly 12 in a variety of different configurations. By way of example, the pinhole apertures may be arranged in the collimator assembly in even rows. In exemplary embodiments, the pinhole apertures 40 may be arranged in the collimator assembly 12 in one, two, three, or more rows or in other ordered or pseudo-random patterns. Those of ordinary skill in the art will appreciate that the pinhole apertures 40 generally define a three-dimensional cone-beam imaging geometry. While the pinhole apertures 40 are illustrated as having a generally circular configuration, those of ordinary skill in the art will appreciate that the pinhole apertures 40 may have any suitable geometry. By way of example, the pinhole apertures 40 may be configured as having aperture configurations that are substantially polygonal (e.g., three-sided, four-sided, five-sided, six-sided, and so forth), or substantially curved (e.g., elliptical, circular, and so forth).

Those of ordinary skill in the art will appreciate that the resolution and sensitivity of the SPECT system 10 is based in part on the cross-sectional area of the adjustable pinhole apertures 40. In general, the pinhole apertures 40 may have the same or different aperture sizes. By way of example, the pinhole apertures 40 may have two or more different cross-sectional areas. Furthermore, as described above, the one or more pinhole apertures 40 have an aperture size that is adjustable. In one exemplary embodiment, the aperture size of the pinholes apertures 40 may be adjusted independently. In another exemplary embodiment, the aperture size of the pinhole apertures 40 may be collectively adjusted. In exemplary embodiments, each of the pinhole apertures 40 may be adjusted to a variety of different widths, for example, from about 0.1 mm to about 10 mm, typically in the range of from about 1 mm to about 5 mm. Further, in certain embodiments, the pinhole apertures 40 may have a length that is generally no more than two or three times greater than the respective widths. The image reconstruction algorithm should appropriately model the system response of the various apertures.

Furthermore, those of ordinary skill in the art will appreciate that the efficiency of gamma ray detection is based on the number of the pinhole apertures 40 in the collimator assembly 12. By way of example, a collimator assembly 12 configured to have a large number of the pinhole apertures 40 would typically require less or no rotation to obtain a sufficient number of angular projections for image reconstruction. Accordingly, the number of the pinhole apertures 40 may be adjusted to provide the desired imaging sensitivity for a desired imaging time. Those of ordinary skill in the art will appreciate that the number and spacing of the pinhole apertures 40 should be chosen with consideration of the efficient utilization of the detector assembly 14 and the performance of the image reconstruction and processing module 18. For example, limited overlap of gamma ray lines of response impacting on the detector assembly 14 may be acceptable.

Figure 3:
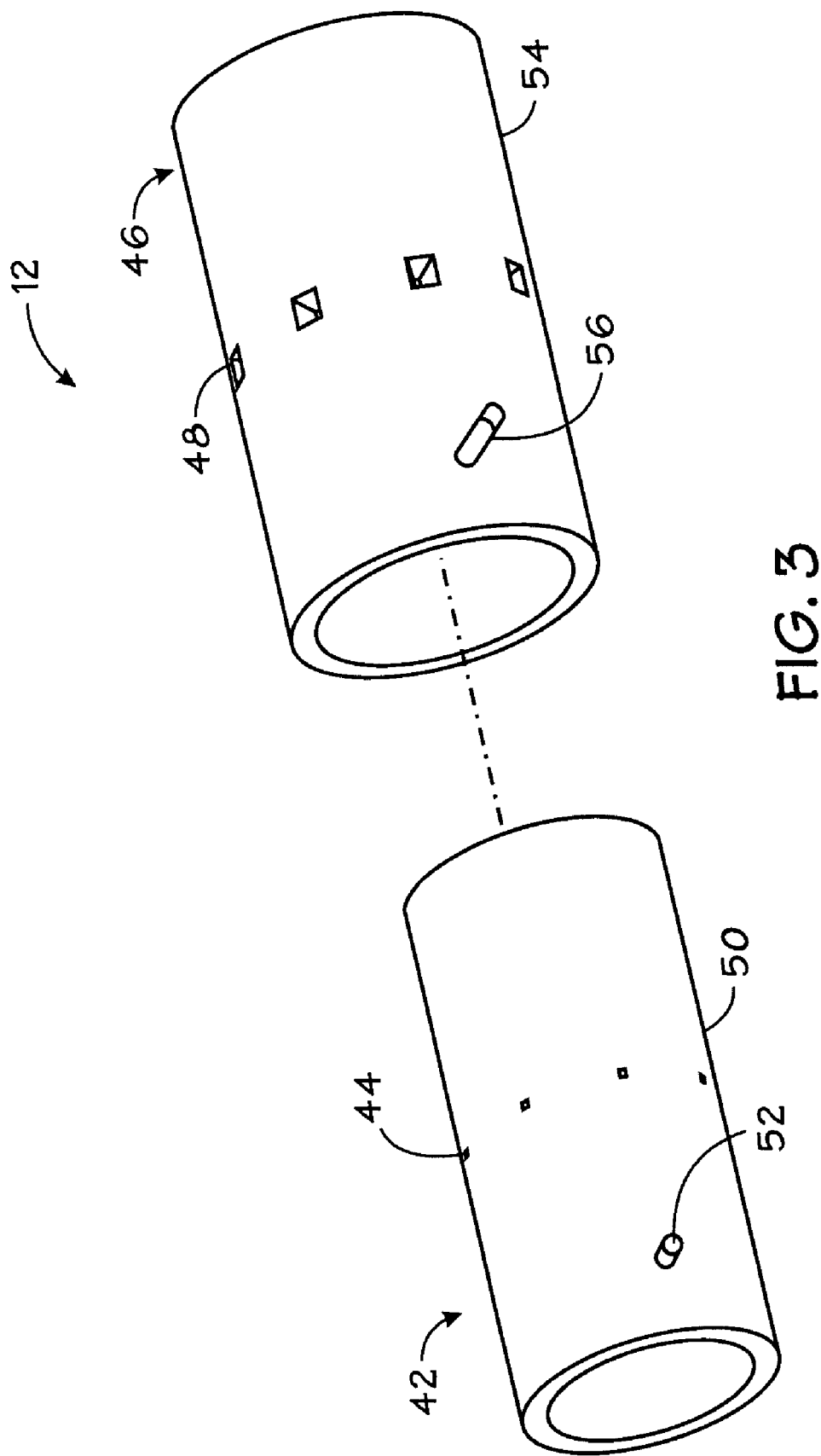
FIG. 3 is an exploded perspective view of an exemplary collimator assembly having one or more adjustable pinhole apertures therein, the collimator assembly including an inner pinhole aperture collimator and an outer pinhole aperture collimator in accordance with embodiments of the present technique.

FIGS. 3-6 illustrate one technique for implementing a collimator assembly 12 having one or more adjustable pinhole apertures 40 therein, in accordance with exemplary embodiments of the present technique. Referring now to FIG. 3, an exploded view of an example collimator assembly 12 having one or more adjustable pinhole apertures 40 therein is illustrated, which may be configured in accordance with exemplary embodiments of the present technique. In the illustrated embodiment, the collimator assembly 12 includes an inner pinhole aperture collimator 42 having one or more inner pinhole apertures 44 therein and an outer pinhole aperture collimator 46 having one or more outer pinhole apertures 48. While FIG. 3 is an exploded view, the collimator assembly 12 may be assembled so that the inner pinhole aperture collimator 42 is disposed closer to the field of view (e.g., field of view 26 on FIG. 1) than the outer pinhole aperture collimator 46.

Moreover, the collimator assembly 12 should be configured so that each of the one or more inner pinhole apertures 44 in the inner pinhole aperture collimator 42 are aligned with a respective one of the one or more outer pinhole apertures 48 in the outer pinhole aperture collimator 46 to define the one or more adjustable apertures 40 in the collimator assembly 12. The aperture size of the one or more adjustable apertures 40 thus defined may be adjusted by relative movement of the inner pinhole aperture collimator 42 and the outer pinhole aperture collimator 46. By way of example, the inner pinhole aperture collimator 42 may rotate with respect to the outer pinhole aperture collimator 46, or vice versa, to adjust the aperture size of the adjustable pinhole apertures 40. Alternatively, the inner pinhole aperture collimator 42 and the outer pinhole aperture collimator 46 may counter-rotate to adjust the aperture size of the adjustable pinhole apertures 40.

The inner pinhole aperture collimator 42 includes one or more inner pinhole apertures 44 therein. While the inner pinhole apertures 44 are illustrated as having a generally square configuration, those of ordinary skill in the art will appreciate that the inner pinhole apertures 44 may have any suitable geometry. By way of example, the inner pinhole apertures 44 may be configured as having aperture configurations that are substantially polygonal (e.g., three-sided, four-sided, five-sided, six-sided, and so forth), or substantially curved (e.g., elliptical, circular, and so forth). Further, the inner pinhole aperture collimator 42 is illustrated as being generally cylindrically shaped. Accordingly, the inner pinhole aperture collimator 42 includes cylindrical body 50 having the one or more inner pinhole apertures 44 therein. Those of ordinary skill in the art will appreciate, however, that the present technique encompasses pinhole aperture collimators that are not generally cylindrically shaped. As will be discussed in more detail below, the inner pinhole aperture collimator 42 further includes an alignment pin 52. In the illustrated embodiment, the alignment pin 52 extends radially from the cylindrical body 50.

The outer pinhole aperture collimator 46 includes one or more outer pinhole apertures 48 therein. While the outer pinhole apertures 48 are illustrated as having a generally square configuration, those of ordinary skill in the art will appreciate that the outer pinhole apertures 48 may have any suitable geometry. By way of example, the outer pinhole apertures 48 may be configured as having aperture configurations that are substantially polygonal (e.g., three-sided, four-sided, five-sided, six-sided, and so forth), or substantially curved (e.g., elliptical, circular, and so forth). Further, the outer pinhole aperture collimator 46 is illustrated as being generally cylindrically shaped. Accordingly, the outer pinhole aperture collimator 46 includes cylindrical body 54 having the one or more pinhole apertures 48 therein. Those of ordinary skill in the art will appreciate, however, that the present technique encompasses pinhole aperture collimators that are not generally cylindrically shaped. For instance, in another embodiment the inner pinhole apertures 44 and the outer pinhole apertures 48 may be rotated about 45 degrees such that the diagonal of the square-shape aperture is aligned with the longitudinal axis and the inner pinhole aperture collimator 42 and the outer pinhole aperture collimator 46 are elliptically shaped to more closely follow the human body's contour. As will be appreciated, elliptically shaped collimator will not be able to rotate with respect to one another so that may be configured to slide axially relative to each other to adjust the size of the pinhole. This technique is not limited to square-shaped pinhole apertures. In this particular embodiment, the rotated square pinholes (rhombus) allow isotropic adjustment of the aperture size in both axial and tangential directions while preserving the square shape.

As will be discussed in more detail below, the outer pinhole aperture collimator 46 further includes an alignment slot 56. In the illustrated embodiment, the alignment slot 56 is sized so that the alignment pin 52 of the inner pinhole aperture collimator 42 may be moveably disposed therein. Those of ordinary skill in the art will appreciate that the use of the alignment pin 52 and the alignment slot 56 represents one of many suitable techniques for maintaining the desired alignment between the inner pinhole apertures 44 of the outer pinhole aperture collimator 42 and the outer pinhole apertures 48 of the outer pinhole aperture collimator 46. By way of example, both the inner pinhole aperture collimator 42 and the outer pinhole aperture collimator 46 may be independently mounted on collimator supports capable of rotating either, or both, collimators. In such an embodiment, the use of the alignment pin 52 and the alignment slot 56 may not be necessary.

Further, the inner and outer pinhole aperture collimators 42 and 46 may be mechanically coupled or placed in contact with each other so as to rotate together, or they may be decoupled so as to rotate separately. In exemplary embodiments, the collimator assembly 12 may be configured to limit movement of the inner pinhole aperture collimator 42 and the outer pinhole aperture collimator 46 with respect to one another. By limiting their respective movement, each of the pinhole apertures 44 in the inner pinhole aperture collimator 42 may remain at least partially aligned with a respective one of the pinhole apertures 48 in the outer pinhole aperture collimator 46. In the illustrated embodiment, the inner pinhole aperture collimator 42 includes an alignment pin 52 that extends radially from the cylindrical body 50 of the inner pinhole aperture collimator 42. The alignment pin 52 is configured to be moveably disposed in the corresponding alignment slot 56 in the cylindrical body 54 of the outer pinhole aperture collimator 46. Accordingly, the alignment pin 52 may be configured to maintain the alignment of the inner pinhole apertures 44 and the outer pinhole apertures 48. Furthermore, the alignment pin 52 illustrated in FIG. 3 is part of the inner pinhole aperture collimator 42 and the alignment slot 56 is part of the outer pinhole aperture collimator 46. Alternatively, the alignment pin 52 may be part of the outer pinhole aperture collimator 46, and the alignment slot 56 may be part of the inner pinhole aperture collimator 42, for example.

Figure 4:
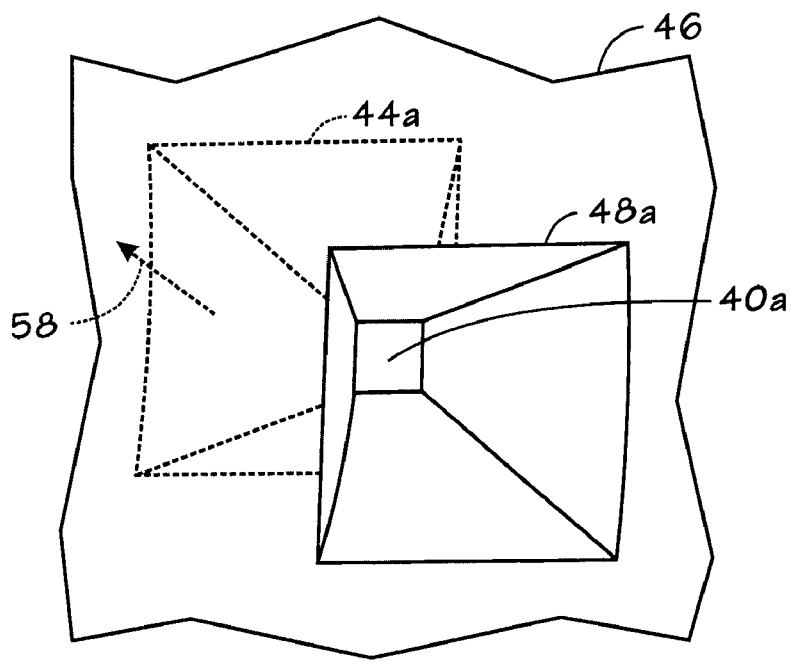
FIGS. 4 and 5 are enlarged views of a portion of a collimator assembly similar to the collimator assembly in FIG. 3 to illustrate an adjustable pinhole aperture in accordance with embodiments of the present technique.
Figure 5:
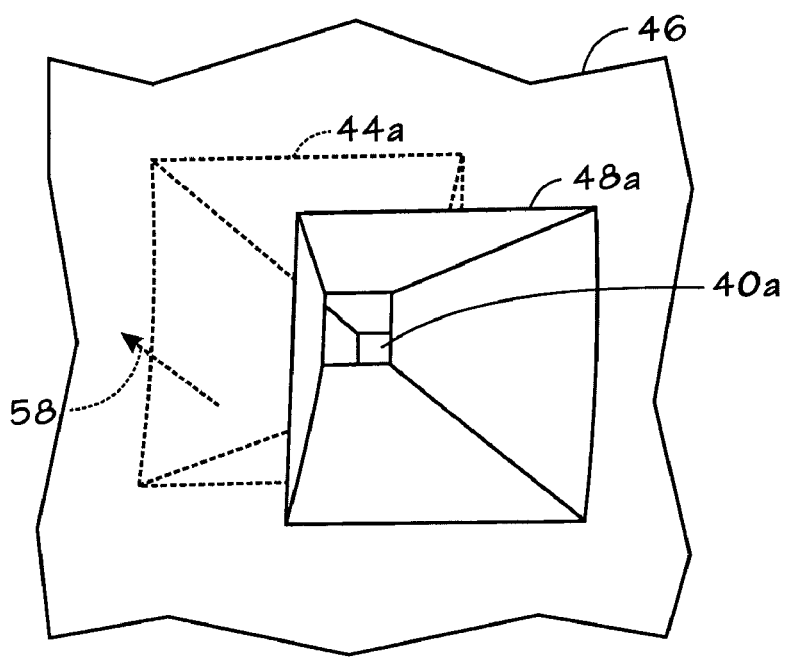

Referring now to FIGS. 4 and 5, a portion of the inner pinhole aperture collimator 42 and a portion the outer pinhole aperture collimator 46 are illustrated in accordance with exemplary embodiments of the present technique. In the illustrated embodiment, an inner pinhole aperture 44a in the inner pinhole aperture collimator 42 is aligned with a respective outer pinhole aperture 48a in the outer pinhole aperture collimator 46 to define an adjustable aperture 40a in the collimator assembly 12. As previously mentioned, movement of at least one of the inner pinhole aperture collimator 42 or the outer pinhole aperture collimator 46 should adjust the aperture size of the pinhole aperture 40a. As illustrated, movement of the outer pinhole aperture collimator 46 in the direction 58 indicated by the arrow adjusts the aperture size of the pinhole aperture 40a. In the illustrated embodiment, the direction 58 of the movement is diagonal with respect to the inner and outer pinhole apertures 44a and 48a. Accordingly, while the aperture size of the adjustable pinhole aperture 40a is adjusted, the pinhole aperture 40a maintains its square shape due to this diagonal movement. Those of ordinary skill in the art will appreciate that movement in directions other than diagonal are encompassed by the present technique.

As illustrated by FIG. 4, when the inner pinhole aperture 44a and the outer pinhole aperture 48a are axially aligned and tangentially aligned, the adjustable pinhole aperture 40a defined thereby has its maximum aperture size. However, as illustrated by FIG. 5, axial displacement of the inner and outer pinhole apertures 44a and 48b results in an adjustable pinhole aperture 40a in the collimator assembly 12 of reduced size. As previously mentioned, the alignment pin 52 in the inner pinhole aperture collimator 42 may limit the movement of the inner pinhole aperture collimator 42 and/or the outer pinhole aperture collimator 46, thus limiting both axial and tangential displacement of the inner and outer pinhole apertures 44a and 48b.

Figure 6:
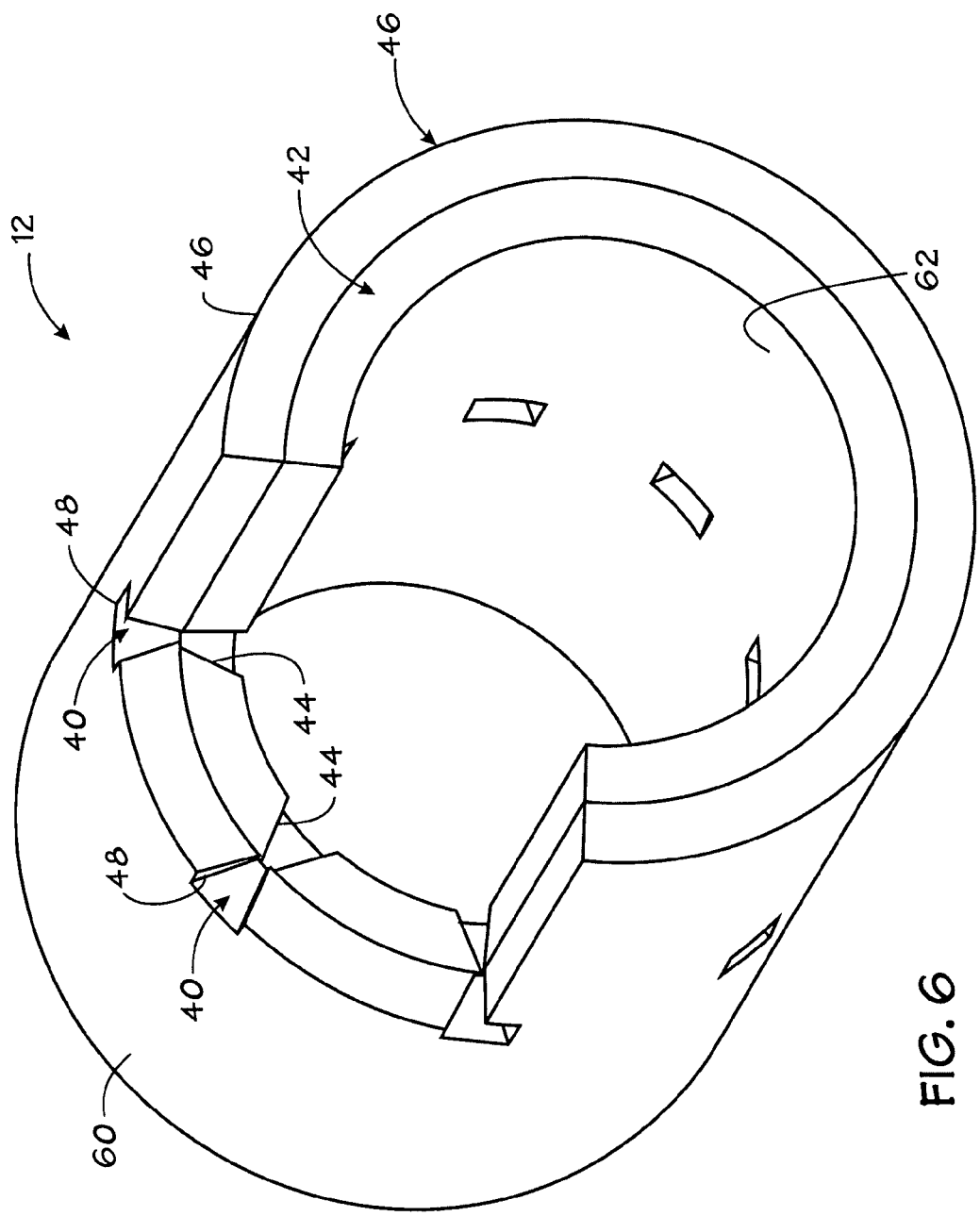
FIG. 6 is a perspective, cut-away view of a collimator assembly similar to the collimator assembly of FIG. 3 to illustrate the adjustable apertures therein in accordance with embodiments of the present technique.

Referring now to FIG. 6, a perspective, cut-away view of the collimator assembly 12 is provided to illustrate the alignment of the inner and outer pinhole apertures 44 and 48, in accordance with exemplary embodiments of the present technique. In the illustrated embodiment, an inner pinhole aperture collimator 42 having one or more inner pinhole apertures 44 therein is disposed within an outer pinhole aperture collimator 46 having one or more outer pinhole apertures 48. As illustrated, the inner and outer pinhole apertures 44 and 48 align to define one or more adjustable apertures 40 in the collimator assembly 12.

In the embodiment of FIG. 6, the outer pinhole apertures 48 open in the shape of a square pyramid to the exterior surface 60 of the outer pinhole aperture collimator 46, and the inner pinhole apertures 44 open in the shape of a pyramid to the inner surface 62 of the inner pinhole aperture collimator 42. With this configuration, gamma rays traveling in a direction oblique to the adjustable pinhole apertures 40 may pass through the collimator assembly 12. Accordingly, gamma rays that pass through the adjustable pinhole apertures 40 would have a square-beam geometry. Gamma rays not aligned with the adjustable pinhole apertures 40 would not pass through the collimator assembly 12. While the inner and outer pinhole apertures 44 and 48 are illustrated as opening in the shape of a pyramid, those of ordinary skill in the art will appreciate that other configurations are encompassed by the present technique. By way of example, the inner and outer pinhole apertures 44 and 48 may open in the shape of a circular cone, for example, if the inner and outer pinhole apertures 44 and 48 have a generally circular configuration.

Figure 7:
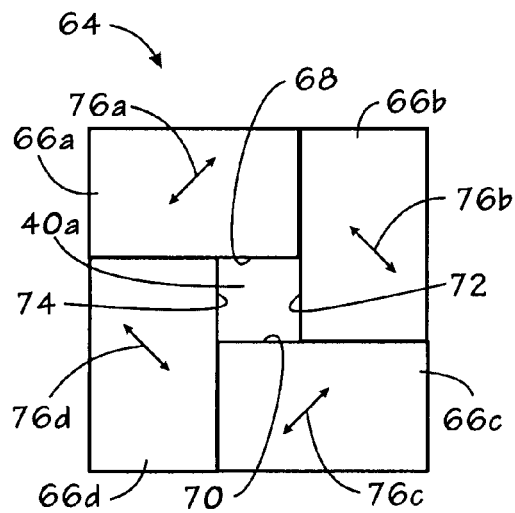
FIGS. 7 and 8 are illustrations of an exemplary diaphragm that includes a plurality of blocks arranged to define an adjustable pinhole aperture in accordance with embodiments of the present technique.
Figure 8:
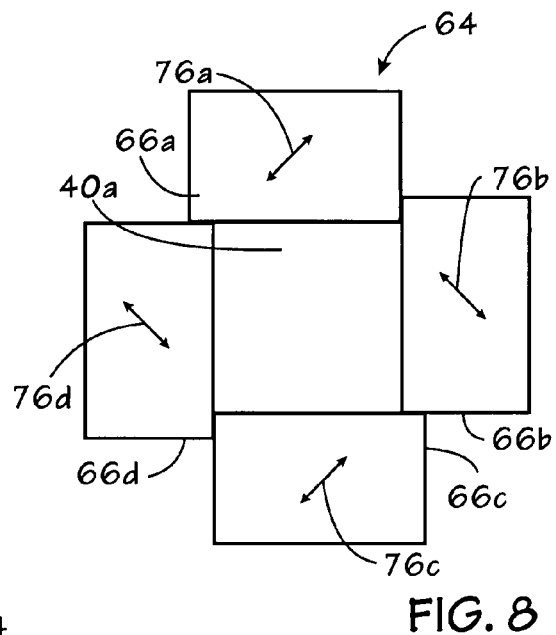

FIGS. 7-14 illustrate an alternative technique for implementing a collimator assembly 12 having one or more adjustable pinhole apertures 40 therein, in accordance with exemplary embodiments of the present technique. Referring now to FIGS. 7 and 8, an exemplary diaphragm 64 that includes a plurality of blocks 66a-66d arranged to define an adjustable pinhole aperture 40a is illustrated. As will be discussed in more detail below with respect to FIG. 14, the diaphragm 64 may be implemented in a collimator assembly 12 to provide a collimator assembly 12 with one or more adjustable pinhole apertures 40. Moreover, the diaphragm 64 is configured so that positioning of the blocks 66a-66d with respect to one another adjusts the aperture size of the adjustable pinhole aperture 40a.

In illustrated embodiment, the diaphragm 64 includes four blocks 66a-66d that are arranged to define an adjustable pinhole aperture 40a having a generally square configuration. As illustrated, blocks 66a and 66c are arranged in parallel and spaced a distance apart to define first and second parallel sides 68 and 70 of the adjustable pinhole aperture 40a. Moreover, blocks 66b and 66d are also arranged in parallel and spaced a distance apart to define third and fourth parallel sides 72 and 74 of the adjustable pinhole aperture 40a. In general, blocks 66b and 66d are generally perpendicular to blocks 66a and 66c. While FIGS. 7 and 8 illustrated four blocks 66a-66d defining a square aperture, any number of blocks may be used and arranged to define an adjustable aperture with a variety of different configurations, including aperture configurations that are substantially polygonal (e.g., three-sided, four-sided, five-sided, six-sided and so forth), or substantially curved (e.g., elliptical, circular and so forth).

As previously mentioned, the positioning of blocks 66a-66d with respect to one another adjusts the aperture size of the adjustable pinhole aperture 40a. By way of example, movement of each of the blocks 66a-66d in the directions 76a-76d indicated by the arrows adjusts the aperture size of the pinhole aperture 40a. In the illustrated embodiment, the directions 76a-76d of the movement are diagonal with respect to the adjustable pinhole aperture 40a. In the illustrated embodiment, the directions 76a-76d of movement of each of the blocks 66a-66d is generally at an angle generally parallel to the diagonals of pinhole aperture 40a. Accordingly, while the aperture size of the adjustable pinhole aperture 40a is adjusted, the adjustable pinhole aperture 40a maintains its square shape due to this diagonal movement. Moreover, each set of two parallel blocks (such as parallel blocks 66a and 66c and parallel blocks 66b and 66d) is move in an opposite direction to adjust the size of pinhole aperture 40a. Similarly, blocks 66b and 66d are also positioned in generally opposite directions with respect to each other. Moreover, the diaphragm 64 may be configured so that parallel blocks 66a and 66c are moved in a direction 76a and 76c that is generally perpendicular to the direction 76b and 76d that parallel blocks 66b and 66d are moved. Further, those of ordinary skill in the art will appreciate that movement of the blocks 66a-66d in directions other than diagonal are encompassed by the present technique. By way of example, moving the blocks 66a-66d from the configuration shown in FIG. 7 to that shown in FIG. 8 may be accomplished by first moving block 66a upward, block 66b rightward, block 66 downward, and block 66d leftward; and then moving block 66a rightward until it touches block 66b, moving block 66b downward until it touches block 66d, moving block 66c leftward until it touches block 66d, and moving block 66d upward until it touches block 66a. In this manner, the net diagonal movement may be accomplished via the vector sum of movements in off-diagonal directions, for example, Referring now to FIG. 9, a side-view of the diaphragm 64 is illustrated. In certain embodiments, adjacent blocks, such as blocks 66d and 66c may be interlocked. In the illustrated embodiment, the edge 78 of the fourth block 66d is configured to interlock with the adjacent edge 80 of the third block 66c. As illustrated, the edge 78 of the fourth block 66d may have a knife edge that interlocks with the adjacent edge 80 of the third block 66c. As illustrated, the adjacent edge 80 of the third block 66c may include an angled recess configured to accept the edge 78 of the fourth block 66d. Those of ordinary skill in the art will appreciate that the interlocking of adjacent blocks 66a-66d of the diaphragm 64 should facilitate the absorption of gamma rays that are not aligned with the adjustable pinhole aperture 40a but are aligned with the intersection of adjacent blocks. Moreover, to permit their positioning, the blocks 66a-66d may be slidably interlocked. As illustrated, blocks 66c and 66d are slidably interlocked. Accordingly, blocks 66c and 66d may be positioned to allow for adjustment of the aperture size of the adjustable pinhole aperture 40a.

Figure 9:
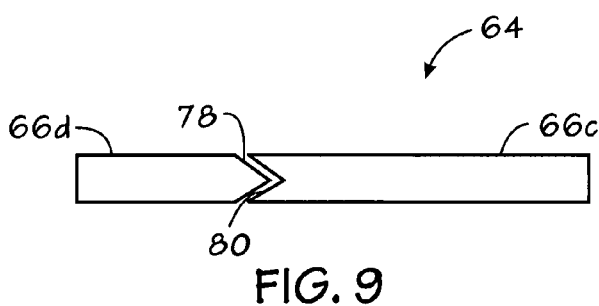
FIG. 9 is a side view of the exemplary diaphragm of FIG. 7 to illustrate the edge configurations of the blocks in accordance with embodiments of the present technique.

Those of ordinary skill in the art will appreciate that the aperture edge of the adjustable pinhole aperture 40a may be defined, for example, by the edges of the blocks 66a-66d. By way of example, an aperture edge (e.g., fourth parallel side 74 on FIG. 7) may be defined by edge 78 of the fourth block 66d, illustrated as a knife edge. While FIG. 9 illustrates the blocks 66a-66d as having a knife-edge configuration, other aperture-edge configurations may also be suitable. Those of ordinary skill in the art will appreciate that the aperture-edge configuration may be selected based on, inter alia, the desired point-spread-function response. Further, the aperture edges may be constructed from the same or different material as that used for the blocks 66a-66d, which may contain a radiation-absorbent material (e.g. lead or tungsten). By way of example, the aperture edges may be made of or coated with gold, tungsten or iridium based, in part, on the desired gamma-ray penetration and x-ray fluorescence properties of the aperture edge.

Figure 10:
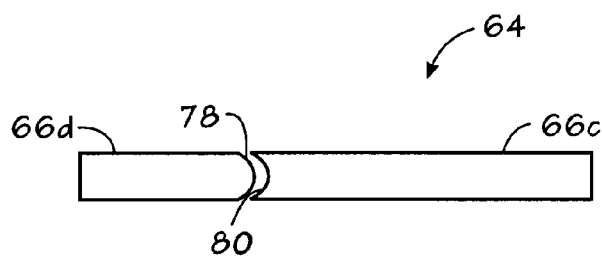
FIG. 10 is a side view of an exemplary diaphragm having blocks with alternative edge configurations to the diaphragm of FIG. 9, in accordance with embodiments of the present technique.

FIG. 10 illustrates a cross-sectional, side view of the diaphragm 64 having an alternative aperture-edge configuration, in accordance with an embodiment of the present technique. As illustrated, the aperture edge (e.g., fourth parallel side 74 on FIG. 7) is defined by edge 78 of the fourth block 66d, illustrates as a round edge. Moreover, the adjacent edge 80 of the third block 66c may be configured to interlock with the edge 78 of the fourth block 66d having a round end. As illustrated, the adjacent edge 80 of the third block 66c that includes a rounded recess 80 configured to accept the edge 78 of the fourth block 66d.

Figure 11:
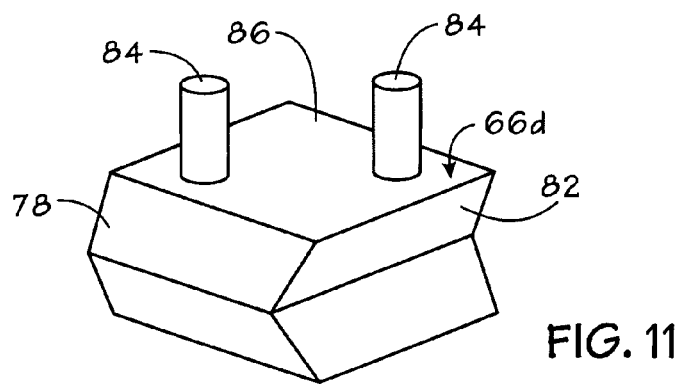
FIG. 11 is a perspective view of one block of the diaphragm of FIG. 7 in accordance with embodiments of the present technique.

Referring now to FIG. 11, an exemplary block 66d of the diaphragm 64 of FIGS. 7 and 8 is illustrated, in accordance with an embodiment of the present technique. In the illustrated embodiment, block 66d has an edge 78 with a knife edge. As previously mentioned, the edge 78 defines the aperture edge (e.g., fourth parallel side 74 on FIG. 7) and interlocks with the adjacent edge 80 of block 66c. Moreover, block 66d also has another edge with an angled recess 82. The angled recess 82 of block 66d may interlock with an edge of the first block 66a that defines an aperture edge (e.g., first parallel side 68 on FIG. 7). Block 66d may further include one or more pins 84 that extend from a surface 86 of the block 66d. In one exemplary embodiment, each of the pins 84 may be coupled to the body of the block 66d to transfer force from an actuator to the block 66d to move the block 66d. Those of ordinary skill in the art should recognize that there are alternative methods that may be utilized to transfer force from an actuator to the block to move it to a desired position.

As previously mentioned, movement of each of the blocks 66a-66d in the directions 76a-76d indicated by the arrows adjusts the aperture size of the adjustable pinhole aperture 40a. A number of different actuators may be used to operate the diaphragm 64. By way of example, any of a variety of different mechanism may be used to position the blocks 66a-66d with respect to one another to adjust the aperture size of the adjustable pinhole aperture 40a, including, for example, a lever-arm mechanism, a rack and pinion mechanism, and so forth.

Figure 12:
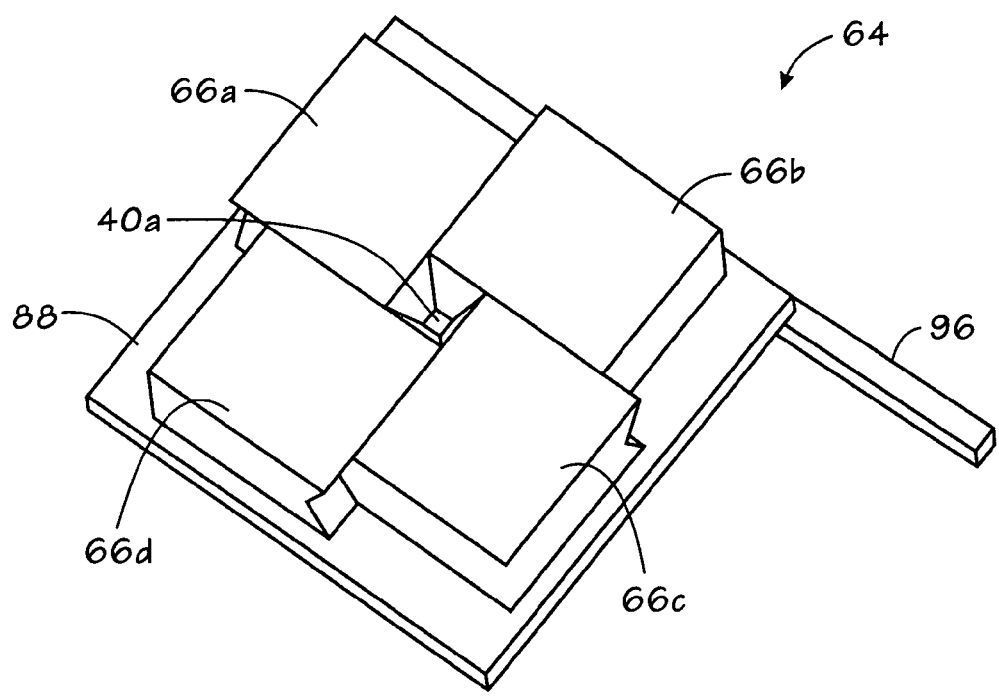
FIG. 12 is a top, perspective view of a diaphragm similar to the diaphragm of FIG. 7 and that includes a lever for adjusting the aperture size in accordance with embodiments of the present technique.
Figure 13:
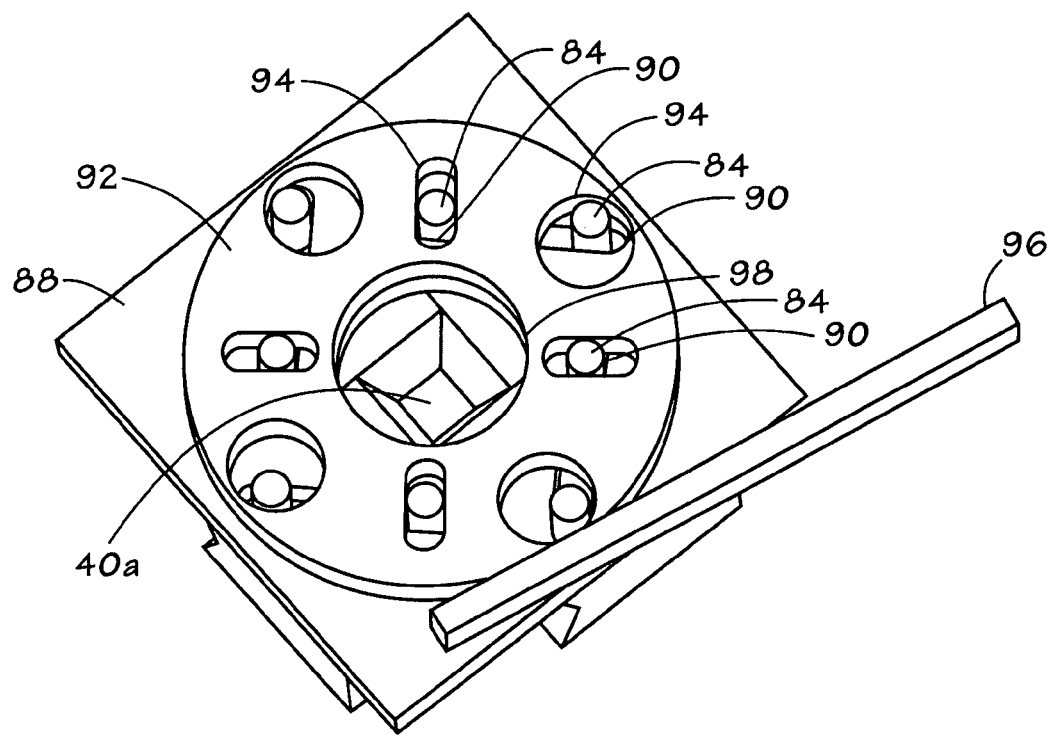
FIG. 13 is another view of the exemplary diaphragm of FIG. 12, in accordance with embodiments of the present technique.

Referring now to FIGS. 12 and 13, an actuator is illustrated for operating the diaphragm 64. In the illustrated embodiment, the actuator includes a lever-arm mechanism configured to move each of the blocks 66a-66d with respect to one another. As illustrated, the lever-arm mechanism includes plate 88, ring 92 and lever 96. Each of the blocks 66a-66d may be coupled to plate 88. Plate 88 includes one or more slots 90 therein. The pins 84 in each of the blocks 66a-66d extend from the surface (e.g., surface 86 on FIG. 11) of the respective block through the corresponding slot. Each of the slots 90 may be sized to define the range of motion of the corresponding block. By way of example, each of the slots 90 may be configured to allow the blocks 66a-66d to move in the directions 76a-76d indicated on FIGS. 7 and 8.

In certain embodiments of the present technique, the ring 92 of the lever-arm mechanism may be coupled, for example, to the plate 88. In one exemplary embodiment, the ring 92 may be rotateably coupled to the plate 88 so that the ring 92 can rotate with respect to the plate 88. As illustrated, the ring 92 may include one or more openings 94 therein for placement of a corresponding one of the pins 84. In the illustrated embodiment, the pins 84 in each of the blocks 66a-66d extend from the surface (e.g., surface 86 on FIG. 11) of the respective block through a corresponding one of the slots 90 in the plate 88 and into a corresponding one of the openings 94 in the ring 92. Each of the openings 94 in the ring 92 may be sized so that rotation of the ring 92 will transfer force to one or more of the pins 84 extending into a corresponding one of the openings 94. In the embodiment illustrated in FIG. 13, certain of the openings 94 are rounded and certain are slotted, wherein the rounded openings are intended for clearance only to allow free movement of the pins 84 inserted therethrough while the slotted openings transmit the force onto the pins 84 as the lever 96 is actuated. For example, the ring 92 may be configured so that sufficient force is transferred to the ring 92 from the lever 96 so that the blocks 66a-66d may move with respect to one another, thus adjusting the aperture size of the pinhole aperture 40a. Further, the ring 92 also may include a central opening 98 therein that is aligned with the adjustable pinhole aperture 40a, for example. In the embodiment illustrated in FIG. 13, the central opening 98 is larger than the maximum desired aperture size of the pinhole aperture 40a to allow unimpeded passage of gamma rays aligned with the pinhole aperture 40a.

The lever 96 of the lever-arm mechanism may be coupled to the blocks 66a-66d. In the illustrated embodiment, the lever 96 may be indirectly coupled to the blocks 66a-66d via ring 92. As illustrated, the lever 96 may be coupled to the ring 92. In general, the lever 96 and the ring 92 may be configured so that movement of the lever 96 rotates the ring 92. As the ring 92 rotates, force may be transferred from the lever 96 to the one or more of the pins 84 of the blocks 66a-66d to move the blocks 66a-66d with respect to one another. In general, the lever 96 may have a range of motion to allow the desired adjustment of the aperture size of the pinhole aperture 40a.

Figure 14:
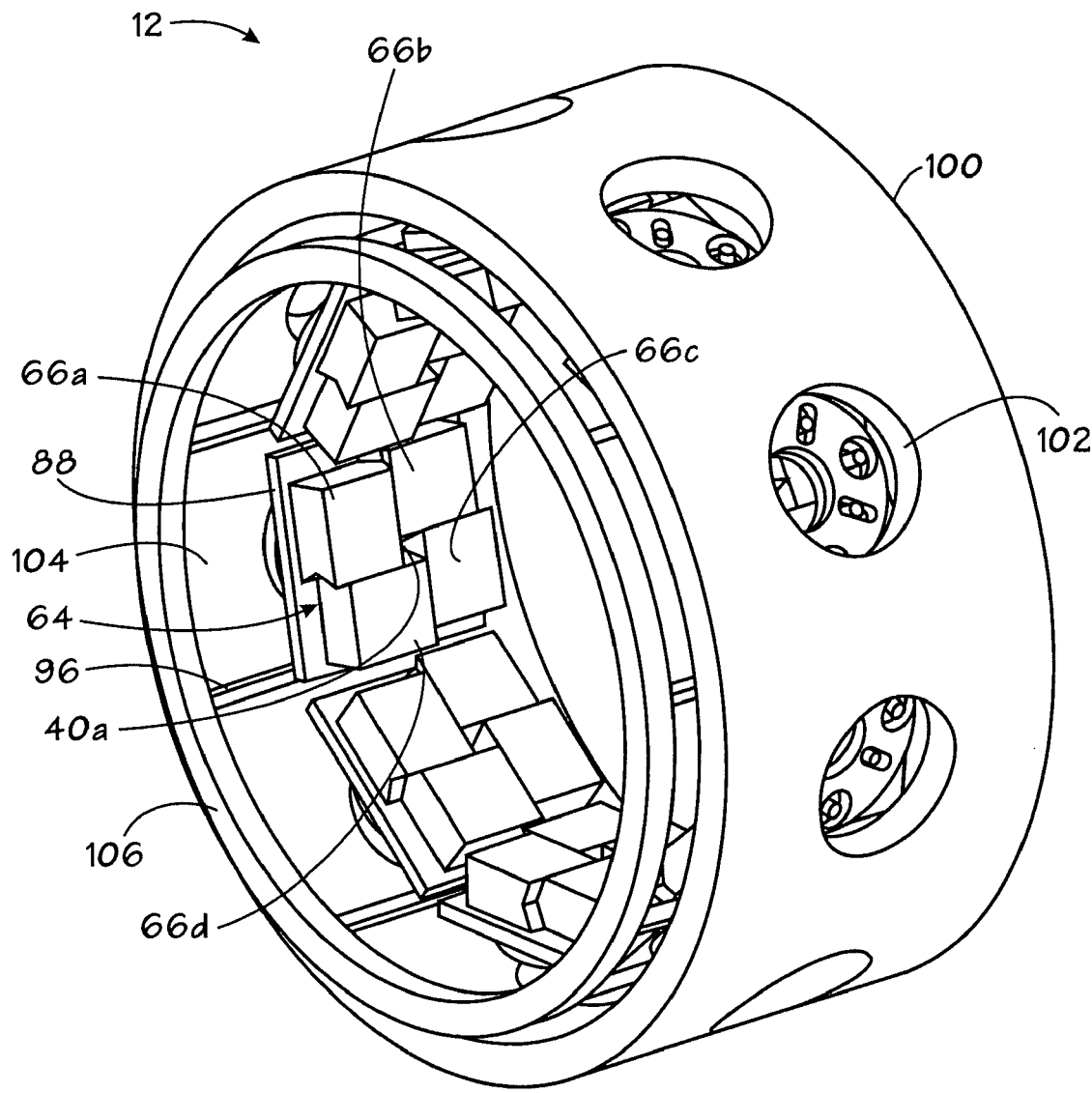
FIG. 14 is a perspective view of another exemplary collimator assembly having one or more adjustable pinhole apertures therein, each of the pinhole apertures defined by a diaphragm similar to the diaphragm of FIG. 7 in accordance with embodiments of the present technique.

As previously mentioned, the diaphragm 64 discussed above with respect to FIGS. 7-13 may be implemented to provide a collimator assembly 12 with one or more adjustable pinhole apertures 40 therein. Referring now to FIG. 14, a collimator 12 is illustrated having one or more diaphragms 64 implemented therein, in accordance with an embodiment of the present technique. In the illustrated embodiment, each of the one or more diaphragms 64 defines a corresponding adjustable pinhole aperture in the collimator assembly 12. As illustrated, the collimator assembly 12 may include a collimator body 100 having one or more openings 102 therein. In the illustrated embodiment, the collimator body 100 serves a dual purpose, as a structure to support each diaphragm 64 and to substantially absorb gamma rays. While the collimator body 100 may taken any of a number of shapes, the collimator body 100 is depicted as generally cylindrical in shape and having a plurality of openings 102 therein. In exemplary embodiments, the openings 102 in the collimator body 100 have an aperture size large than the largest desired aperture size of the adjustable pinhole apertures 40, for example, to allow unimpeded passage of gamma rays aligned with the pinhole apertures 40.

As described above, each of the diaphragms implemented into the collimator assembly 12 may include a plurality of blocks arranged to form an adjustable pinhole aperture. For example, diaphragm 64 includes four blocks 66a-66d that are arranged to form adjustable pinhole aperture 40a. Moreover, each of the diaphragms may be arranged in the collimator assembly 12 so that each of the adjustable pinhole apertures 40 (such as pinhole aperture 40a on FIG. 14) is aligned with a corresponding one of the openings 102 in the collimator body 100. Accordingly, gamma rays that are aligned with the adjustable pinhole apertures 40 pass through the openings 102 and do not contact the collimator body 100. In the illustrated embodiment, each of the blocks that define one of the adjustable pinhole apertures 40 is coupled to a corresponding plate. By way of example, blocks 66a-66d may be coupled to the plate 88. Further, the plate 88 may be coupled to an inner surface 104 of the collimator body 100. The plate 88 may be positioned in the collimator assembly 12 to align each of the adjustable pinhole apertures 40 with a corresponding one of the openings 102 in the collimator body 100.

In accordance with exemplary embodiments, any suitable actuator may be utilized for operating each of the diaphragms (e.g., diaphragm 64) in the collimator assembly. In the illustrated embodiment, the actuator includes a lever-arm mechanism coupled to an actuator ring 106. As illustrated, each of the diaphragms includes a corresponding lever coupled to blocks defining the adjustable pinhole aperture. By way of example, lever 96 may be coupled to blocks 66a-66d, as described above. Each of the levers (e.g., lever 96) may be coupled to the actuator ring 106. Accordingly, movement of the actuator ring 106 results in corresponding movement of the levers. As described above, the levers may be coupled to the blocks defining the adjustable pinhole apertures so that movement of the levers results in a corresponding movement of the blocks and thus an adjustment of the aperture size. By way of example, movement of the actuator ring 106 should result in movement of the lever 96, thus resulting in movement of the blocks 66a-66d with respect to one another. The blocks 66a-66d should be arranged so that movement thereof results in adjusting the aperture size of the adjustable pinhole aperture 40a. In another embodiment, the actuating mechanism may involve the rings 106 and the lever 96 decoupled from the ring 92. The lever 96 may be placed with a rack rod, and the ring 92 may function as a pinion (round edge replaced with a gear shape). Thus, by pushing on the ring 96 in the direction of the main axis of the collimator assembly 12, the rack and pinion mechanism that includes the rod 96 and gear on the ring 92 will actuate ring 92 and, in turn, will actuate on pins 84 to effectuate movement of blocks 66a-66d.

III. Exemplary Slit Aperture Collimator Embodiments

Figure 15:
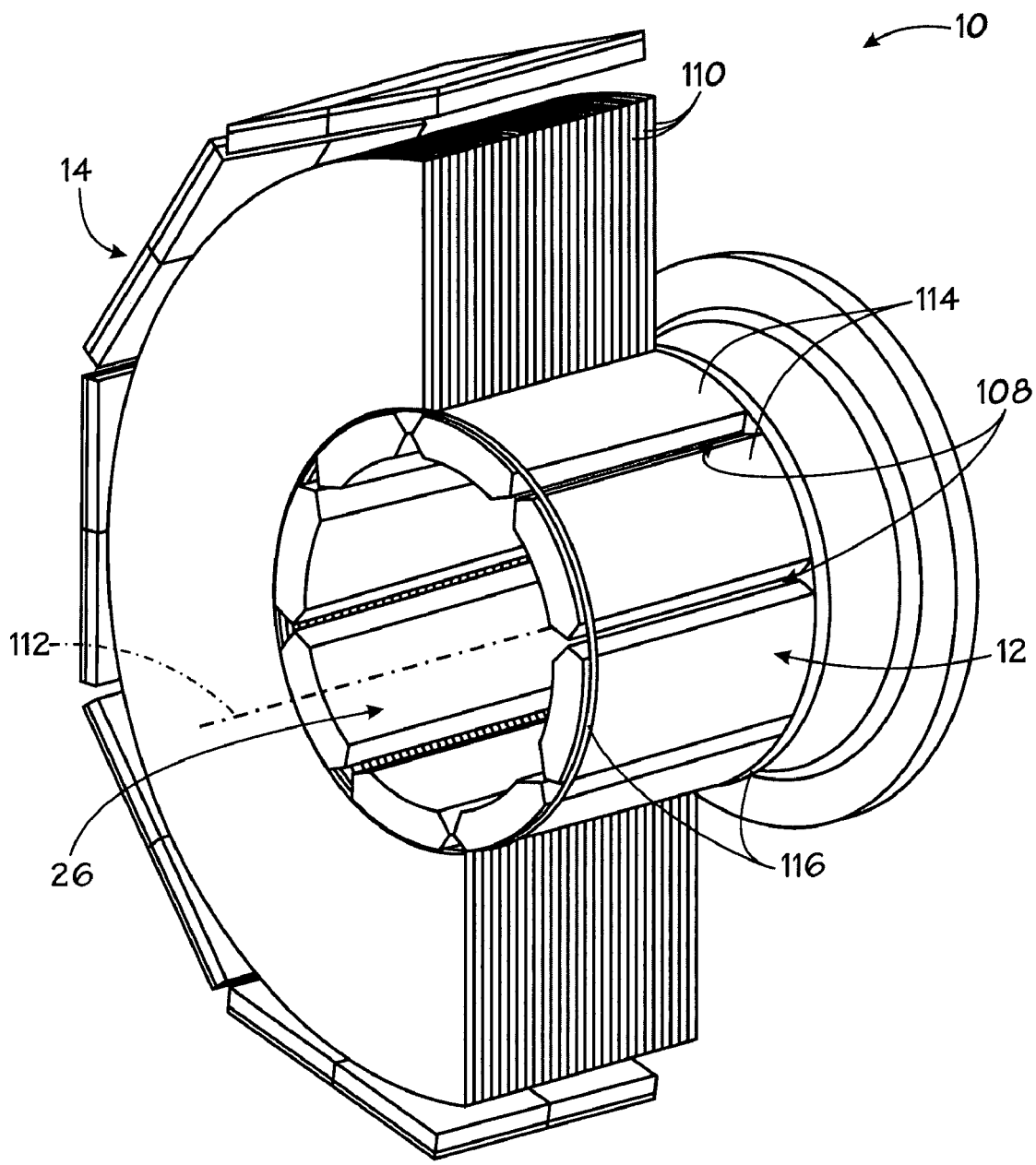
FIG. 15 is a perspective view of an exemplary SPECT system that includes a slit aperture collimator in accordance with embodiments of the present technique.

While the preceding discussion of FIGS. 2-14 has described adjustable pinhole aperture collimators, the present technique is also applicable to slit aperture collimator. Referring now to FIG. 15, a perspective view of the collimator assembly 12 with a detector assembly 14 encircling the collimator assembly 12 is provided, in accordance with exemplary embodiments of the present technique. As illustrated, a portion of the detector assembly 14 is removed to illustrate the components of the collimator assembly 12, particularly the one or more slit apertures 108 and the one or more septa 110. In general, the collimator assembly 12 and the one or more septa 110 may be arranged such that the one or more slit apertures 108 and the one or more septa 110 define one or more pathways for gamma rays emanating from a subject placed in the field of view 26. Gamma rays aligned with one of the slit/septa pathways should pass through the collimator assembly 12, while gamma rays that are not aligned with one of the slit/septa pathways should not pass through the collimator assembly. Those of ordinary skill in the art will appreciate that the slit apertures 108 and the septa 110 generally define a two-dimensional fan-beam imaging geometry wherein the septa 100 generally define transaxial slices.

As illustrated, the slit apertures 108 may extend in a direction generally parallel to the longitudinal axis 112 of the collimator assembly 12. In addition, the collimator assembly 12 may include one or more sections spaced around the longitudinal axis 112 of the collimator assembly 12 such that spaces between the sections define the slit apertures 108. By way of example, the spaced sections may be or include one or more panels 114 spaced around the longitudinal axis 112 of the collimator assembly 12 so as to define the slit apertures 108.

Moreover, the slit apertures 108 are referred to as generally one dimensional because the length of a slit aperture 108 is typically long in comparison to the width of the slit aperture 108. For example, the length of a slit aperture 108 may be four, five, ten, or more times greater than the respective width of the slit aperture 108.

For support, the panels 114 may be coupled by a mechanical coupling mechanism, such as bands (rings) 116 illustrated on FIG. 15. By way of example, each of the bands 116 may be coupled to each of the panels 114 at the respective ends of the collimator assembly 12. As illustrated, the bands 116 may be configured to hold the panels 114 in a generally cylindrical arrangement. Alternatively, a collar or other suitable assembly may be used to hold the panels 114 in the desired arrangement. Further, while the panels 114 are illustrated in FIG. 2 as curved sections, the present technique encompasses the use of sections that are not curved. In addition, while the panels 114 of the collimator assembly 12 are illustrated as separate sections, the present technique encompasses the use of a collimator assembly 12 that is unitary. That is, the collimator assembly 12 may be fabricated as a solid piece having one or more slit apertures 108 therein. Furthermore, in certain exemplary embodiments, the collimator assembly 12 may be constructed as a unitary piece in which the slit apertures 108 are filled by a material that provides mechanical support but that also allows most gamma rays to pass through the slit apertures 108 without interaction.

As previously mentioned, one or more septa 110 may be spaced on a side of the collimator assembly 12 opposite from the field of view 26. In the illustrated embodiment, each of the septa 110 is generally annular-shaped and spaced along the longitudinal axis 112 of the collimator assembly 12. The septa 110 may be arranged, for example, to provide the desired slice information for the SPECT system 10. As illustrated, the septa 110 are generally parallel to each other and generally perpendicular to the longitudinal axis 112 of the collimator assembly 12. In this embodiment, the septa 110 may define the axial slice information for the SPECT system 10 while the adjustable slit apertures 108 provide the transaxial information. Those of ordinary skill in the art will appreciate that the septa 110 may also be arranged in a generally converging or diverging configuration to alter the slice definition by either magnifying or minifying the axial field of view.

Those of ordinary skill in the art will appreciate that the resolution and sensitivity of the SPECT system 10 is based in part on the width of the adjustable slit apertures 108 and the septa 110 spacing. In general, the width of the adjustable slit apertures 108 and the septa 110 spacing may be the same or different, with different widths providing different resolving power. By way of example, the adjustable slit apertures 108 and the spacing between each of the septa 110 may have two or more different widths. As previously mentioned, the adjustable slit apertures 108 have aperture sizes that are adjustable. In exemplary embodiments, the adjustable slit apertures 108 may be adjusted to a variety of different widths, for example, in the range of from about 0.1 mm to about 10 mm, and typically in the range of from about 1 mm to about 5 mm. Furthermore, the adjustable slit apertures 108 may be configured for collective and/or independent adjustment. Adjustment of the adjustable slit apertures 108 to have different widths may provide widths with different resolving power and sensitivities. By differing the aperture size of the adjustable slit apertures 108, the spatial resolution and sensitivities of the SPECT system 10 may be changed. In certain embodiments, the spacing between the septa 110 may have a width in the range of from about 0.1 mm to about 10 mm, and typically in the range of from about 1 mm to about 5 mm. The various adjustable slit apertures 108 and septa 110 spacing may have a distribution of sizes, and thus differing spatial resolutions and sensitivities. The image reconstruction algorithm should appropriately model the system response of the various apertures.

Furthermore, those of ordinary skill in the art will appreciate that the efficiency of gamma ray detection is based on the number of slit apertures 108 in the collimator assembly 12. By way of example, a collimator assembly 12 configured to have a large number of slit apertures 108 would typically require less or no rotation to obtain a sufficient number of angular projections for image reconstruction. Accordingly, the number of the slit apertures 108 may be adjusted to provide the desired imaging sensitivity for a desired imaging time. Those of ordinary skill in the art will appreciate that the number and spacing of the slit apertures 108 should be chosen with consideration of the efficient utilization of the detector assembly 14 and the performance of the image reconstruction and processing module 18. For example, limited overlap of gamma ray lines of response impacting on the detector assembly 14 may be acceptable.

While the preceding discussion of FIG. 15 has described the slit apertures in the collimator assembly as having slit apertures 108 extending in a direction generally parallel to the longitudinal axis 112 of the collimator assembly 12, and the septa 110 spaced along the longitudinal axis 112 of the collimator assembly 12, one of ordinary skill in the art will recognize that the present technique may be implemented with collimator assemblies having alternative slit configurations. By way of example, the slit apertures 108 may extend in a direction generally perpendicular to the longitudinal axis 112 of the collimator assembly 12 while the septa 110 may extend longitudinally and radially from the collimator assembly 12. In another exemplary embodiment, the slit apertures 108 may extend in a direction generally diagonal to the longitudinal axis 112 of the collimator assembly 12, for example, the slit apertures 108 may follow spirals.

Figure 16:
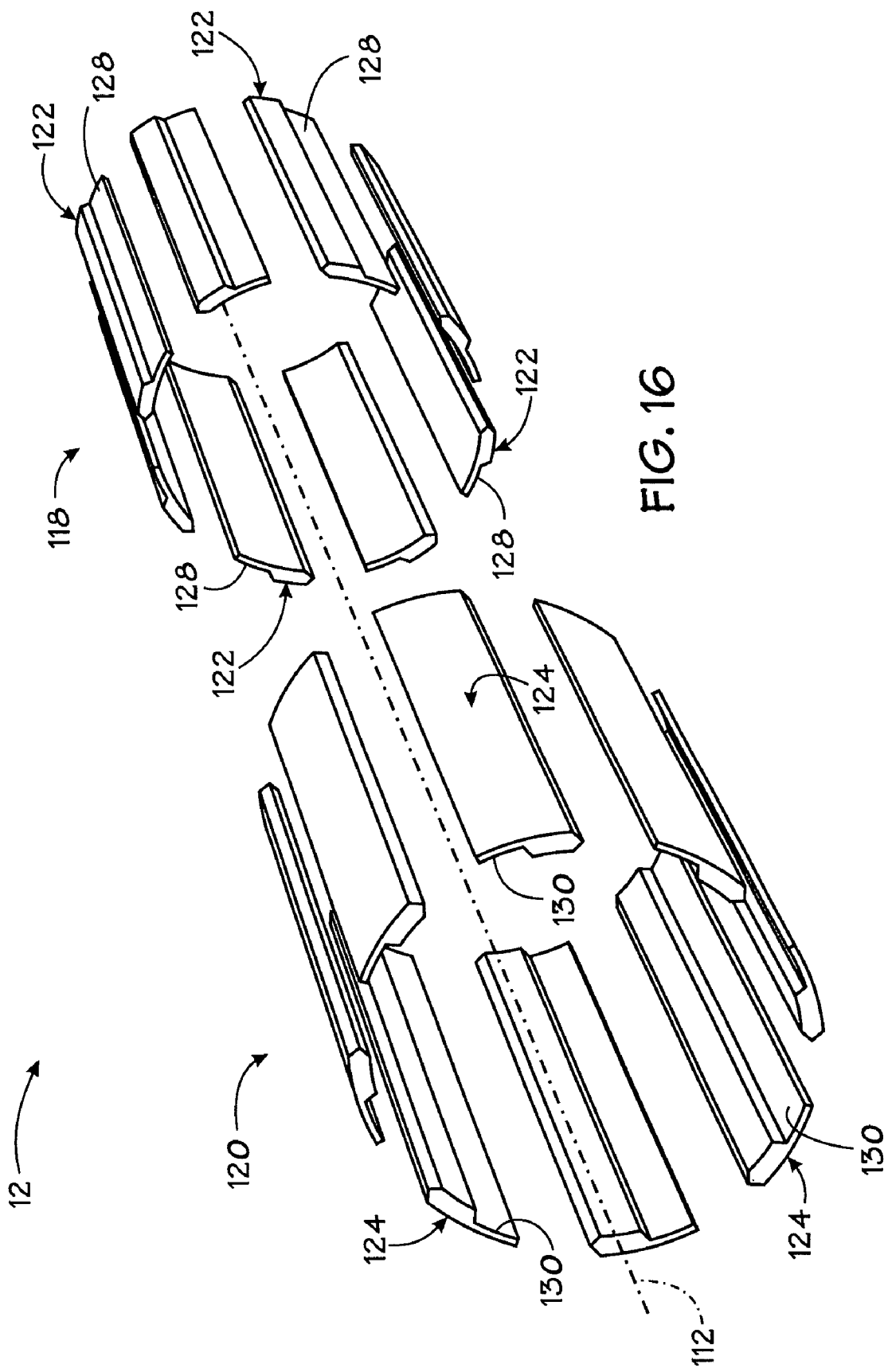
FIG. 16 is an exploded perspective view of exemplary collimator assembly having one or more adjustable slit apertures therein, the collimator assembly including an inner and outer collimator in accordance with embodiments of the present technique.
Figure 17:
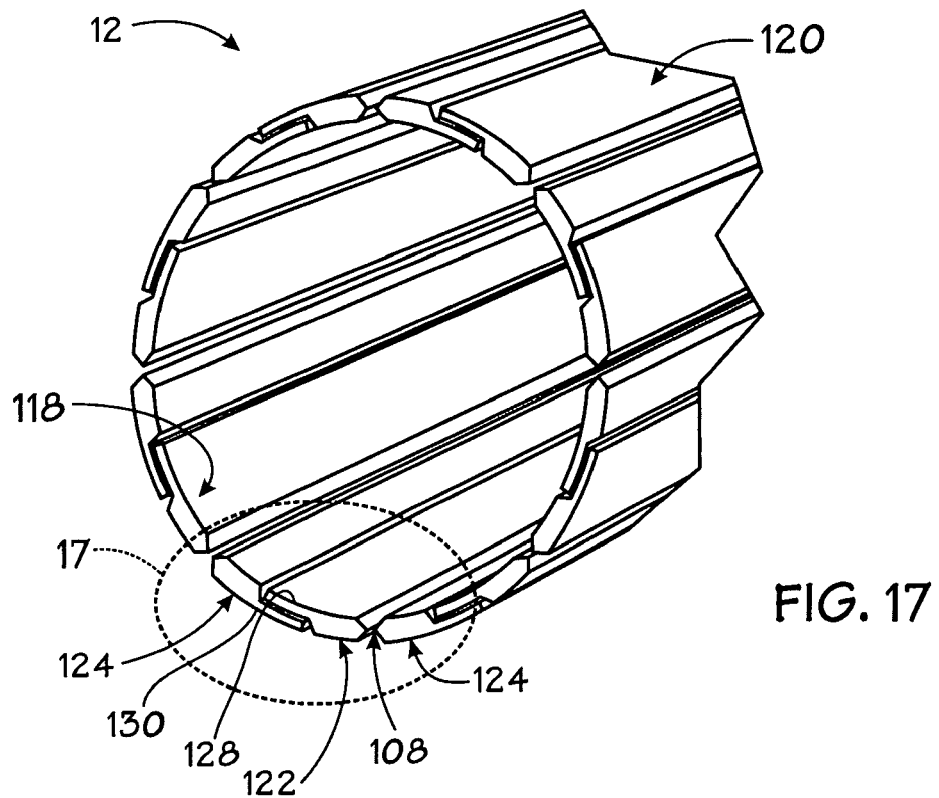
FIG. 17 is a perspective view of a portion of the exemplary collimator assembly of FIG. 16 in accordance with embodiments of the present technique.
Figure 18:
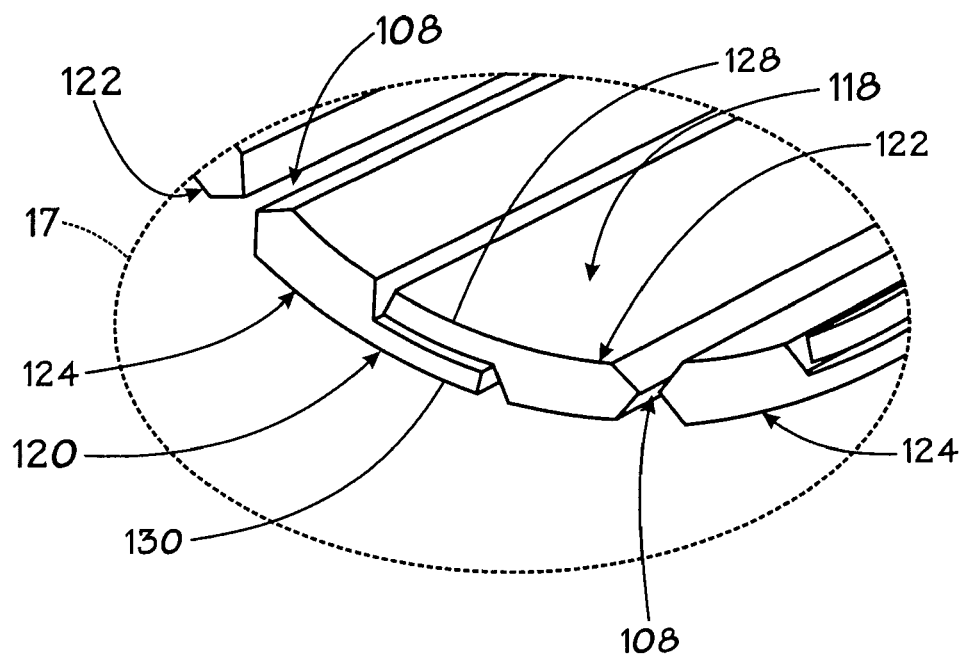
FIG. 18 is an enlarged view of a portion of the exemplary collimator assembly of FIG. 17 taken along line 17 in accordance with embodiments of the present technique.

FIGS. 16-18 illustrate one technique for implementing a collimator assembly 12 having one or more adjustable slit apertures 108 therein, in accordance with exemplary embodiments of the present technique. Referring now to FIG. 16, an exploded view of an example collimator assembly 12 having one or more slit apertures 108 therein is illustrated, which may be configured in accordance with exemplary embodiments of the present technique. In the illustrated embodiment, the collimator assembly 12 includes an inner cylindrical slit collimator 118 and an outer cylindrical slit collimator 120. While FIG. 16 is an exploded view, the collimator assembly 12 may be assembled so that the inner cylindrical slit collimator 118 is disposed closer to a volume (such as field of view 26 on FIG. 15) than the outer cylindrical slit collimator 120. As will be described in more detail below, the inner cylindrical slit collimator 118 and the outer cylindrical slit collimator 120 each include a plurality of overlapping panels, such as inner panels 122 and outer panels 124, wherein spaces between adjacent inner and outer panels 122 and 124 define the adjustable slit apertures 108, as illustrated by FIGS. 17-18. In general, the inner cylindrical slit collimator 118 and the outer cylindrical slit collimator 120 should be configured so that relative rotation of the inner cylindrical slit collimator 118 and the outer cylindrical slit collimator 120 adjusts the aperture size of the adjustable slit apertures 108. By way of example, the inner cylindrical slit collimator 118 may rotated with respect to the outer cylindrical slit collimator 120 or vice versa.

The inner cylindrical slit collimator 118 includes a plurality of inner panels 122 spaced at least partially around the longitudinal axis 112 of the collimator assembly 12. In the illustrated embodiment, the inner panels 122 extend in a direction generally parallel to the longitudinal axis 112 of the collimator assembly 12. Further, each of the inner panels 122 includes a thinned portion 128 extending along the length of the respective panel. In general, the thinned portion 128 of a respective panel has a thickness less than the remainder of the panel. As illustrated, the inner panels 122 are spaced around the longitudinal axis 112 of the collimator assembly 12 such that the thinned portion 128 of the inner panels 122 are not adjacent to one another. For support, the inner panels 122 may be coupled by any suitable mechanical coupling mechanism, such as bands (rings) or collars (not illustrated). By way of example, bands may be coupled to each of the inner panels 122 at the respective ends of the collimator assembly 12. In exemplary embodiments, the bands may be configured to hold the inner panels 122 in a generally cylindrical arrangement. Further, while the inner panels 122 are illustrated in FIG. 16 as curved sections, the present technique encompasses the use of panels that are not curved.

The outer cylindrical slit collimator 120 includes a plurality of outer panels 124 spaced at least partially around the longitudinal axis 112 of the collimator assembly 12. In the illustrated embodiment, the outer panels 124 extend in a direction generally parallel to the longitudinal axis 112 of the collimator assembly 12. Further, each of the outer panels 124 includes a thinned portion 130 extending along the length of the respective panel. In general, the thinned portion 130 of a respective panel has a thickness less than the remainder of the panel. As illustrated, the outer panels 124 are spaced around the longitudinal axis 112 of the collimator assembly 12 such that the thinner portion 130 of the outer panels 124 are not adjacent to one another. For support, the outer panels 124 may be coupled by any suitable mechanical coupling mechanism, such as bands (rings) or collars (not illustrated). By way of example, bands may be coupled to each of the outer panels 124 at the respective ends of the collimator assembly 12. In exemplary embodiments, the bands may be configured to hold the outer panels 124 in a generally cylindrical arrangement. Further, while the outer panels 124 are illustrated in FIG. 16 as curved sections, the present technique encompasses the use of panels that are not curved.

As previously mentioned, the inner cylindrical slit collimator 118 and the outer cylindrical slit collimator 120 may be assembled so that spaces between adjacent inner and outer panels 122 and 124 define one or more adjustable slit apertures 108. Referring now to FIGS. 17 and 18, a collimator assembly 12 is illustrated having an inner cylindrical slit collimator 118 disposed within an outer cylindrical slit collimator 120. In the illustrated embodiment, the inner cylindrical slit collimator 118 and the outer cylindrical slit collimator 120 each include a plurality of overlapping panels, such as inner panels 122 and outer panels 124, wherein spaces between adjacent inner and outer panels 122 and 124 define the one or more adjustable slit apertures 108. For example, the inner cylindrical slit collimator 118 and the outer cylindrical slit collimator 120 should be arranged so that each of the inner panels 122 is adjacent to two of the outer panels 124. Each of the inner panels 122 should overlap with one of the adjacent outer panels 124. As illustrated, the thinned portion 128 of one of the inner panels 122 overlaps with the thinned portion 130 of one of the outer panels 124.

In addition, the inner cylindrical slit collimator 118 and the outer cylindrical slit collimator 120 should be configured so that rotation of at least one of the inner cylindrical slit collimator 118 or the outer cylindrical slit collimator 120 adjusts the aperture size of the adjustable slit apertures 108. In exemplary embodiments, rotation of the inner cylindrical slit collimator 118 with respect to the outer cylindrical slit collimator 120, or vice versa, should increase or decrease the aperture size of the adjustable slit apertures 108. For example, clockwise rotation of the inner cylindrical slit collimator 118 with respect to the outer cylindrical slit collimator 120 should increase the size of the adjustable slit apertures 108. Moreover, counter-rotation of the inner cylindrical slit collimator 118 and the outer cylindrical slit collimator 120 should also increase or decrease the aperture size of the adjustable slit apertures 108. Moreover, the width of the thinned portions 128 and 130 of the inner and outer panels 122 and 124, respectively, may define the range of motion for rotation of at least one of the inner cylindrical slit collimator 118 or the outer cylindrical slit collimator 120. By way of example, rotation of the inner cylindrical slit collimator 118 with respect to the outer cylindrical slit collimator 120 will be limited by width of the thinner portions 128 and 130.

Figure 19:
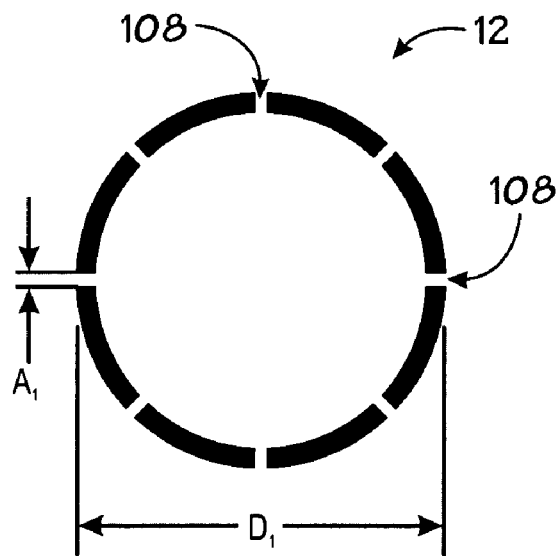
FIGS. 19 and 20 are illustrations of another exemplary collimator assembly having a plurality of adjustable slit apertures therein in accordance with embodiments of the present technique.
Figure 20:
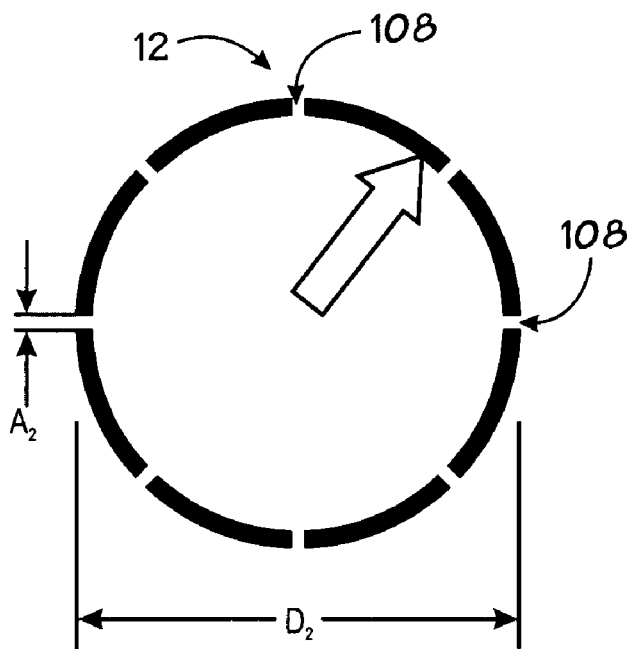

FIGS. 19 and 20 illustrate an alternative technique for implementing a collimator assembly 12 having one or more adjustable slit apertures 108 therein, in accordance with exemplary embodiments of the present technique. In the illustrated embodiment, the collimator assembly 12 is generally cylindrical in shape and has adjustable slit apertures 108 therein. The collimator assembly 12 may be configured to have an adjustable diameter, wherein adjustment of the diameter results in a corresponding aperture size adjustment. By way of example, the adjustable slit apertures 108 may have a first aperture size A1 at a first diameter D1 of the collimator assembly 12 and a second aperture size A2 at a second diameter D2 of the collimator assembly 12. In exemplary embodiments, the collimator assembly 12 may be configured so that dilation of the collimator assembly 12 increases the aperture size of the adjustable slit apertures 108 and/or contraction of the collimator assembly 12 decreases the aperture size of the adjustable slit apertures 108. As illustrated by FIGS. 19 and 20, dilation of the collimator assembly 12 from a diameter of D1 to a diameter of D2 results in a corresponding increase in aperture size from A1 to A2. Those of ordinary skill in the art will appreciate that the technique illustrated by FIGS. 19 and 20 for aperture size adjustment may be implemented with a variety of different slit aperture collimators. For example, this technique may be implemented with collimator assembly 12 illustrated on FIG. 15 that includes a plurality of panels 114 arranged to define a plurality of adjustable slit apertures 108. Those of ordinary skill in the art will appreciate that the combined thickness of the inner and outer panels 112 and 124 should be sufficient to stop gamma rays of the desired energy for SPECT imaging. In particular, when the panels are rotated to adjust the slit aperture size, a pathway may be exposed in which gamma rays would pass only through the thinned section of one of the panels. If the thickness of the thinned panel section is not sufficient to stop the gamma rays, then additional radiation absorbent material may be need to block passage of gamma rays not aligned with the slit apertures. This additional material could be added to the outer and/or inner panels 122 and 1234 in the region where the panels transition from full thickness to thinned thickness, for example, and in such as way as to not interfere with relative rotation of the collimator panels.

Figure 21:
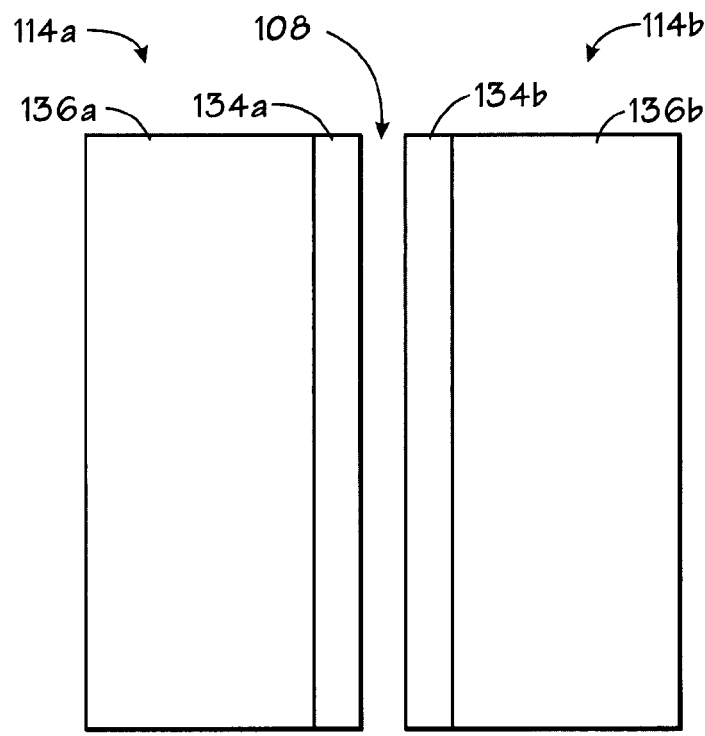
FIG. 21 is an illustration of two panels of a slit aperture collimator that define an adjustable slit aperture in accordance with embodiments of the present technique.
Figure 22:
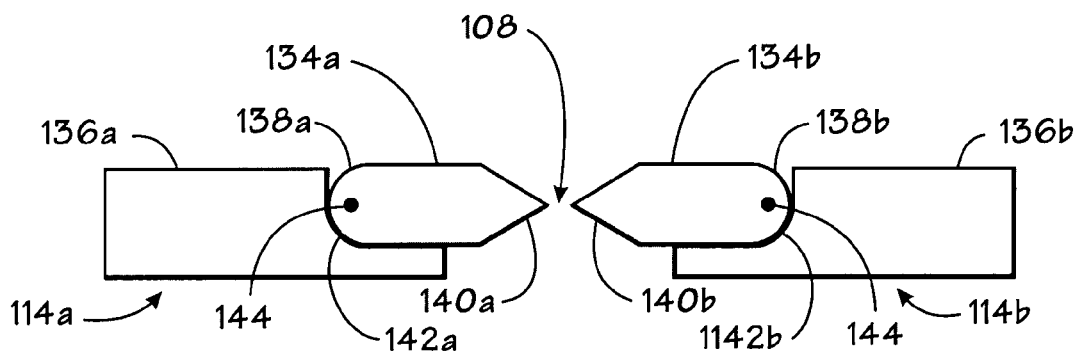
FIGS. 22 and 23 are side views of an adjustable slit aperture similar to the adjustable slit aperture of FIG. 21 in accordance with embodiments of the present technique.
Figure 23:
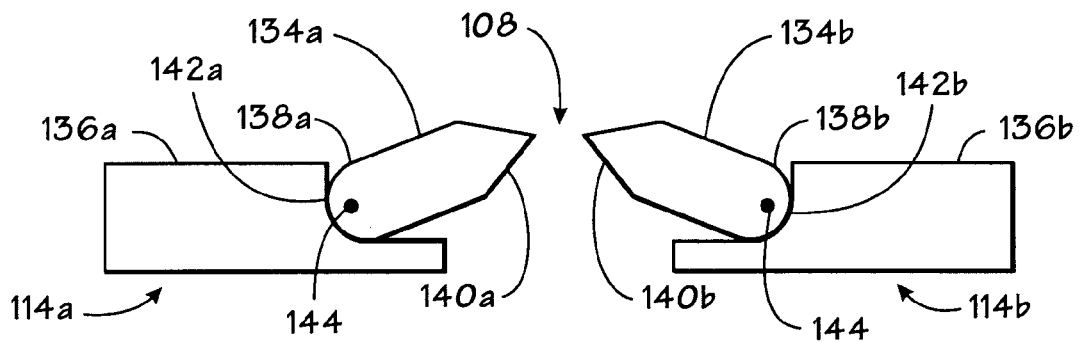

FIGS. 21-23 illustrate another alternative technique for implementing a collimator assembly 12 having one or more adjustable slit apertures 108 therein, in accordance with exemplary embodiments of the present technique. In the illustrated embodiment, panels 114a and 114b define adjustable slit aperture 108. As previously described and illustrated by FIG. 15, a plurality of panels 114 (e.g., panels 114a and 114b) may be arranged at least partially around the longitudinal axis 112 of a collimator assembly 12 and extending in a direction generally parallel thereto with the spaces between the panels 114 defining each adjustable slit aperture 108. Referring again to FIGS. 21-23, the panels 114 may be configured such that rotation of the slit edges 134 (e.g., slit edges 134a and 134b) adjusts the aperture size of the adjustable slit aperture 108, as will be discussed in more detail below, In the illustrated embodiment, the panels 114 include panel bodies 136 (e.g., panel bodies 136a and 136b) and slit edges 134. As illustrated, the slit edges 134 are the portion of the panels 114 that are adjacent to the adjustable slit aperture 108. The space between the slit edges 134 defines the adjustable slit aperture 108. In exemplary embodiments, the slit edges 134 may have rounded ends 138 (e.g., rounded ends 138a and 138b) and knife ends 140 (e.g., knife ends 140a and 140b). The rounded ends 138 of the slit edges 134 may overlap with a portion of the panel bodies 136. In the illustrated embodiment, the rounded ends 138 may be configured to mate with a corresponding recess (such as rounded recesses 142a and 142b) of the panel bodies 136. As illustrated the rounded recesses 142 of the panel bodies 136 may be at one end of the panel bodies 136. While FIGS. 22 and 23 illustrate the slit edges 134 as having a knife-edge configuration, other aperture edge configurations (e.g., rounded) may also be suitable. Those of ordinary skill in the art will appreciate that the aperture edge configuration may be selected based on, inter alia, the desired point-spread-function response. Further, the slit edges 134 may be constructed from the same or different material as that used for the panel bodies 136, which may contain a radiation-absorbent material, such as lead or tungsten, for example.

As previously mentioned, rotation of the slit edges 134 may adjust the aperture size of the adjustable slit aperture 108. By way of example, rotation of at least one of slit edge 134a or slit edge 134b should adjust the aperture size of the adjustable slit aperture 108. In the illustrated embodiment, rotation of the knife edges 140 of the slit edges 134 adjusts the aperture size of the adjustable slit aperture 108. In exemplary embodiments, the knife edges 140 rotate with respect to the corresponding rounded ends 138. As illustrated, the knife edges 140 rotate about an axis of rotation, illustrated on FIGS. 22 and 33 as pins 144. Pins 144 may extend at least partially through the length of the slit edges 134. In exemplary embodiments, pins 144 may extend through the length of the rounded ends 138 of the slit edges 134. While not illustrated, an end of the pins 144 may extend beyond the ends of the slit edges 134 wherein rotation of the pins 144 results in relative rotation of the knife edges 140. By way of example, the end of the pins 144 may be configured as a gear with a corresponding actuator to facilitate rotation of the pins 144.

Figure 25:
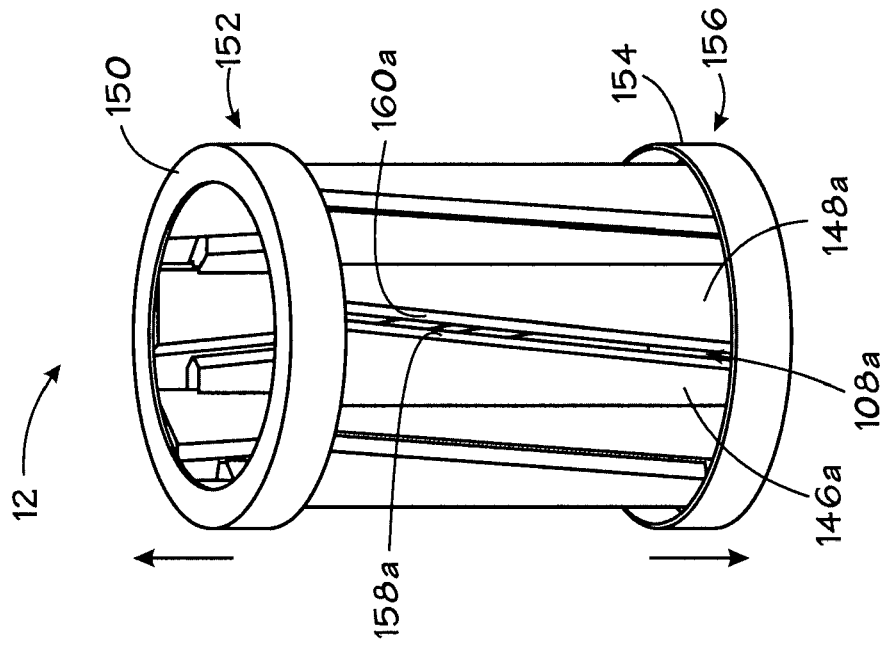
FIG. 25 is a perspective view of the collimator assembly of FIG. 24 to illustrate adjustment of slit aperture size in accordance with embodiments of the present technique.
Figure 24:
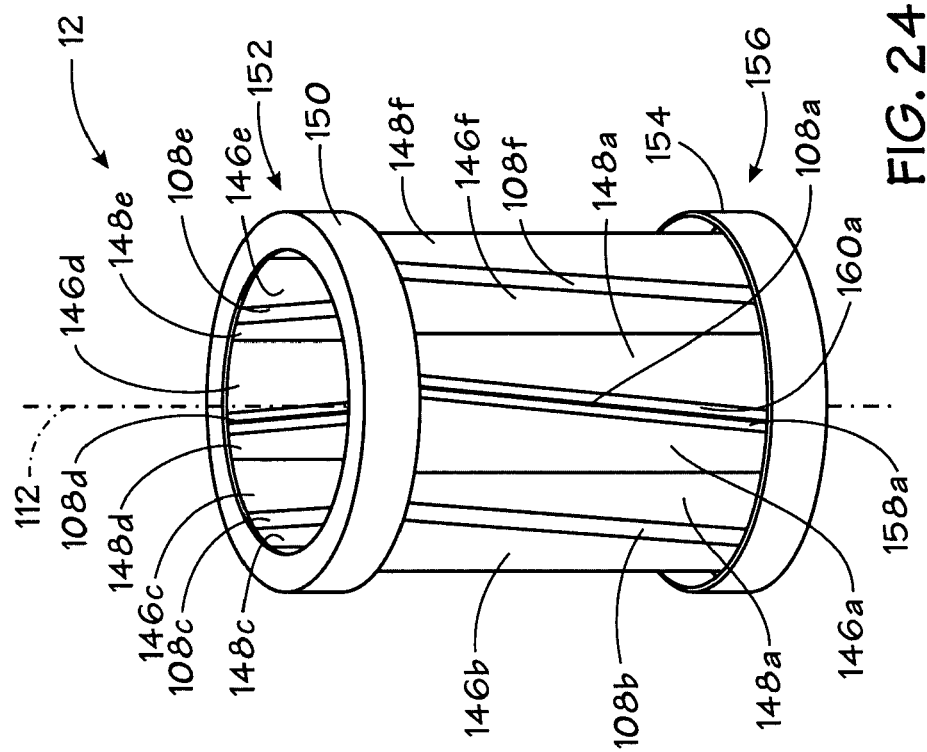
FIG. 24 is a perspective view of another exemplary collimator assembly having one or more adjustable slit apertures therein, the collimator assembly including a first set of panels and a second set of panels in accordance with embodiments of the present technique.

FIGS. 24-28 illustrate another alternative technique for implementing a collimator assembly 12 having one or more adjustable slit apertures 108 therein, in accordance with exemplary embodiments of the present technique. Referring now to FIGS. 24 and 25, the collimator assembly 12 may include a first set of panels 146 (e.g., panels 146a-146f) and a second set of panels 148 (e.g., panels 148a-148f). While the first set of panels 146 and the second set of panels 148 are illustrated as each including six panels, those of ordinary skill in the art will appreciate that the present technique encompasses the use of more or less panels. As illustrated, the first set of panels 146 and the second set of panels 148 may be arranged at least partially around the longitudinal axis 112 of the collimator assembly 12 so that spaces between the first set of panels 146 and the second set of panels 148 define one or more adjustable slit apertures 108 (e.g., adjustable slit apertures 108a-108f) therein. As will be discussed in more detail below, the collimator assembly 12 may be configured so that axial movement of at least one of the first set of panels 146 or the second set of panels 148 adjusts the aperture size of the adjustable slit apertures 108.

The first set of panels 146 and the second set of panels 148 may extend in a direction generally parallel to the longitudinal axis 112 of the collimator assembly. Moreover, in exemplary embodiments, the first set of panels 146 and the second set of panels 148 may be arranged around the longitudinal axis 112 in a generally polygonal configuration. Further, the first set of panels 146 and the second set of panels 148 may be arranged in an alternating pattern so that each of the first set of panels 146 is adjacent to two of the second set of panels 148 and vice versa. By way of example, panel 146a of the first set of panels 148 is adjacent to panels 148a and 148b of the second set of panels 148. In the illustrated embodiment, the first set of panels 146 are coupled to a top ring 150 (e.g., a collar) at a first end 152 of the collimator assembly 12, and the second set of panels 148 are coupled to a bottom ring 154 (e.g., a collar) at a second end 156 of the collimator assembly 12, the second end 156 being opposite from the first end 152.

As previously mentioned, the first set of panels 146 and the second set of panels 148 may be arranged around the longitudinal axis 112 of the collimator assembly 12 so that spaces between the first set of panels 146 and the second set of panels 148 define one or more adjustable slit apertures 108 therein. For example, panel 146a of the first set of panels 146 and panel 148a of the second set of panels 148 may be arranged such that a space between the adjacent panels defines the adjustable slit aperture 108a. In general, each of the panels in the first set of panels 146 and the second set of panels 148 has a slit edge 158 (e.g., slit edges 158a of panel 146a) and opposing slit edges 160 (e.g., opposing slit edge 160a of panel 148a). As illustrated, the slit edge 158a of panel 146a and the opposing slit edge 160a of panel 148a are the portions of the respective panels that are adjacent to the adjustable slit aperture 108a. As will be discussed in more detail below, the side of the slit edges 158 and the opposing slit edges 160 may be angled with respect to the panel's axis.

In exemplary embodiments, axial movement of at least one of the first set of panels 146 or the second set of panels 148 adjusts the aperture size of the adjustable slit apertures 108. By way of example, the collimator assembly 12 may be configured to allow top ring 150 and bottom ring 154 to move along the longitudinal axis 112 of the collimator assembly 112. Accordingly, movement of at least one of the top ring 150 or bottom ring 154 in a direction away from each other along the longitudinal axis 112 should enlarge the adjustable slit apertures 108. In a similar manner, movement of at least one of the top ring 150 or the bottom ring 154 in a direction toward each other along the longitudinal axis 112 should reduce the size of the adjustable slit apertures 108. As illustrated by FIGS. 24 and 25, the adjustable slit apertures 108 should enlarge as the top ring 150 and bottom ring 154 are moved away from each other along the longitudinal axis 112 of the collimator assembly 12.

Figure 26:
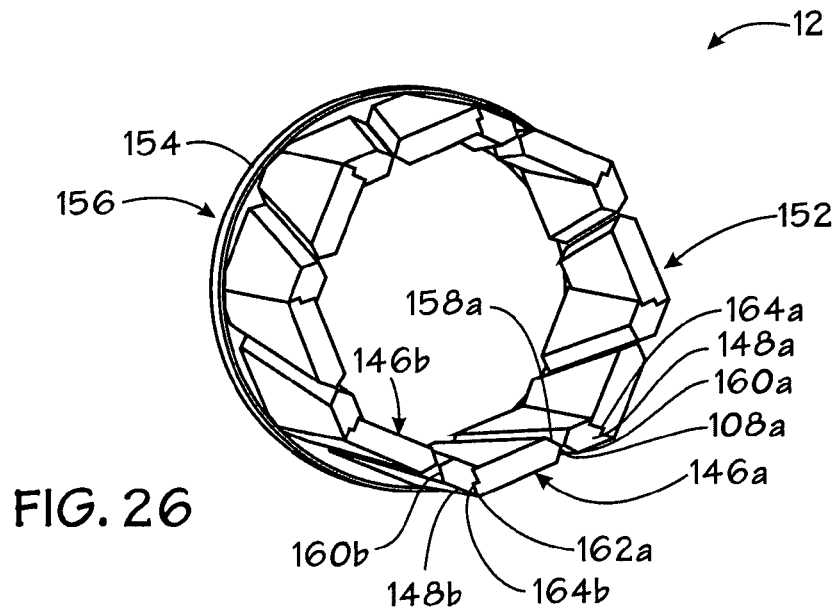
FIG. 26 is an end view of the collimator assembly of FIG. 24 in accordance with embodiments of the present technique.

Referring now to FIG. 26, a top view of a collimator assembly 12 similar to the collimator assembly of FIGS. 24 and 25 is illustrated, in accordance with embodiments of the present technique. As illustrated, the top ring 150 at the first end 152 of the collimator assembly 12 is removed to illustrate the first set of panels 146 and the second set of panels 148. In the illustrated embodiment, each of the panels includes a slit edge and an interlocking side. For example, panel 146a of the first set of panels 146 includes a slit edge 158a and an interlocking side 162a. As previously mentioned, the space between the slit edge 158a of panel 146a of the first set of panels 146 and the opposing slit edge 160a of panel 148a of the second set of panels 148 defines an adjustable slit aperture 108a. Furthermore, the opposite side (e.g., interlocking side 162a) of one of the first set of panels 146 may be interlocked with an opposing side (e.g., opposing interlocking side 164b) one of the second set of panels 148. As illustrated, the interlocking side 162a of panel 146a may be interlocked with the opposing interlocking side 164b of panel 148b. Moreover, to permit axial movement of at least one of the first set of panels 146 or the second set of panels 148, the panels may be slidably interlocked. Accordingly, at least one of the first set of panels 146 or the second set of panels 148 may be moved along the longitudinal axis 112 of the collimator assembly 12 for adjustment of the aperture size of the adjustable slit apertures 108.

While FIG. 26 illustrates the slit edges 158 and the opposing slit edges 160 as having a knife-edge configuration, other aperture edge configurations (e.g., rounded) may also be suitable. Those of ordinary skill in the art will appreciate that the aperture edge configuration may be selected based on, inter alia, the desired point-spread-function response.

Figure 27:
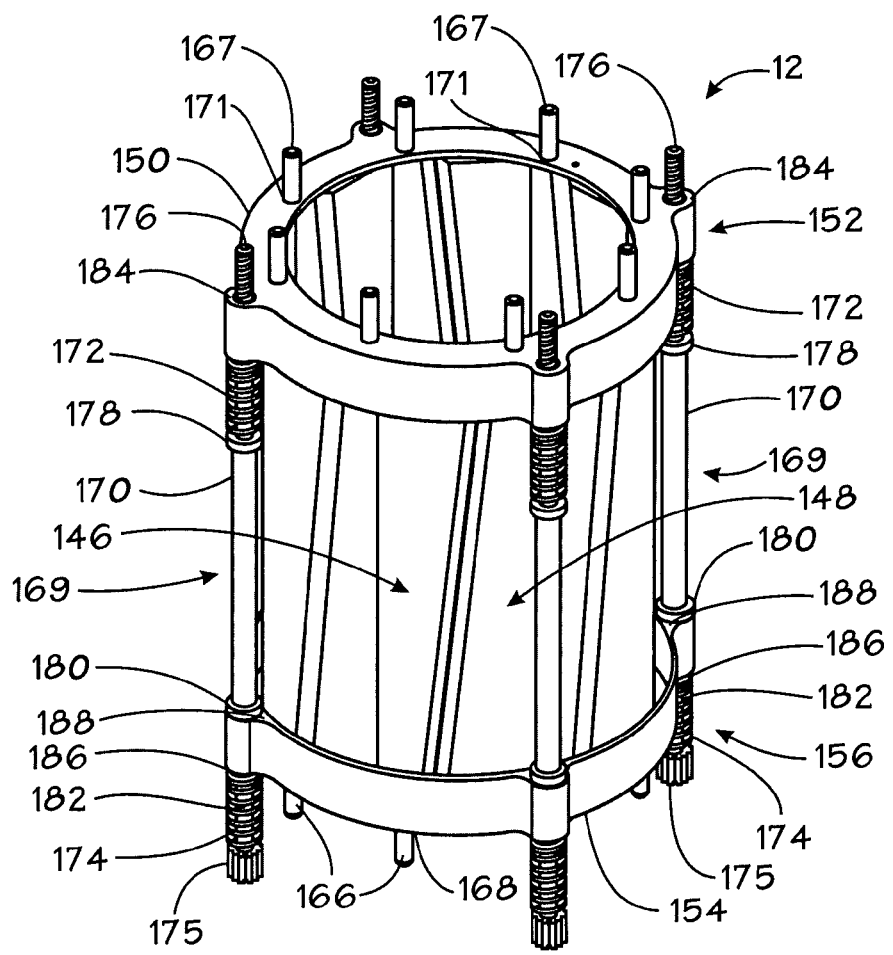
FIG. 27 is a perspective view of a collimator assembly similar to the collimator assembly of FIG. 24 and having side rods for positioning the first and second set of panels in accordance with embodiments of the present technique.

Referring now to FIG. 27, a perspective view of a collimator assembly 12 similar to the collimator assemblies of FIGS. 24-26 is illustrated, in accordance with embodiments of the present technique. In the illustrated embodiment, the first set of panels 146 have first alignment pins 166 extending therefrom on the second end 156 of the collimator assembly 12, and the second set of panels 148 have second alignment pins 167 extending therefrom on the first end 152 of the collimator assembly 12. As illustrated, the first alignment pins 166 may be coupled to the end of the first set of panels 146 that is opposite the end that is coupled to the top ring 150. Further, the second alignment pins 167 may be coupled to the end of the second set of panels 148 that is opposite the end that is coupled to the bottom ring 154. When the collimator assembly 12 is assembled, the first alignment pins 166 on the second end 156 of the collimator assembly 12 may be disposed in corresponding first pin openings 168 in the bottom ring 154. In a similar manner, the second alignment pins 167 on the first end 152 of the collimator assembly 12 may be disposed in corresponding second pin openings 171 in the top ring 150. Among other things, the first and second alignment pins 166 and 167 may facilitate relative alignment of the top ring 150 and bottom ring 154 and alignment of the first and second set of panels 146 and 148.

As illustrated in FIG. 27, the collimator assembly 12 may further include rod assemblies 169. In general, the rod assemblies 169 may be used to axially position the top ring 150 and/or the bottom ring 154 so as to adjust the aperture size of the adjustable slit apertures 108. In the illustrated embodiment, the rod assemblies 169 include rods 170, top springs 172, bottom springs 174, and gears 175. In exemplary embodiments, each of the rods 170 include a threaded portion 176, a top collar 178, a bottom collar 180, and a lower end 182. As illustrated the threaded portion 176 is located on the opposite end of each of the rods 170 from the lower end 182. The top collar 178 is located between the threaded end 176 and the bottom collar 180. The bottom collar 180 is located between the top collar 178 and the lower end 182.

In the illustrated embodiment, rod assemblies 169 are located on the periphery of the collimator assembly 12 and are disposed generally parallel to the longitudinal axis 112 of the collimator assembly 12. The threaded end 176 of each of the rods 170 may be threaded through a corresponding threaded rod opening 184 in the top ring 150. The top springs 172 are disposed over the rods 170 between the threaded rod opening 184 and the top collar 178. In exemplary embodiments, the top springs 172 may be pre-loaded to prevent backlash of the upper ring 150 and, in turn, backlash of the second set of panels 148. The lower end 182 of each of the rods 170 may be disposed in a corresponding rod opening 186 in the bottom ring 154. Lower springs 174 may be disposed over the lower end 182 of the rods 170 between the rod opening 186 and the gears 175. The bottom ring 154 may be configured to allow for rotation of the rods 170. The rods 170 generally should not slide through the rod opening 186 when assembled as the rods 170 should be constrained by lower collar 180 and bottom springs 174. In exemplary embodiments, the bottom springs 174 may be pre-loaded to prevent undesired movement of the bottom ring 154 and, in turn, undesired motion of the first set of panels 146.

As described above, the rod assemblies 169 may be used to axially position the top ring 150 and/or the bottom ring 154 so as to adjust the aperture size of the adjustable slit apertures 108. In general, a common gear (not illustrated) may be used to drive the gears 175. Rotation of the gears 175 results in respective rotation of the rod assemblies 169, resulting in axial separation of the top ring 150 and the bottom ring 154. In the illustrated embodiment, counter-clockwise rotation (as viewed from below) of the rod assemblies 169 should result in upward movement of the top ring 150 and, in turn, upward movement of the first set of panels 146. As the first set of panels 146 are driven upward the size of the adjustable slit apertures 108 should increase. In a similar manner, clockwise rotation (as viewed from below) of the rod assemblies 169 should result in downward movement of the top ring 150 and, in turn, downward movement of the first set of panels 146. As the first set of panels 146 are driven downward the size of the adjustable slit apertures 108 should decrease. In this manner, the rod assemblies 169 may be used to adjust the aperture size of the adjustable slit apertures 108. As will be appreciated, while the preceding description discussion of clockwise and counter-clockwise assumes a right-hand thread on rod 170, the present technique also encompasses other thread configurations, such as a left-hand thread.

The collimator assembly 12 illustrated by FIGS. 24-28 may be assembled via any suitable technique. In accordance with one embodiment, the first set of panels 146 and the second set of panels 148 may be coupled to the top ring 150 and the bottom ring 154, respectively. Each of rods 170 may be inserted through the corresponding rod openings 186 in the bottom ring 154 until the bottom collar 180 of each of the rods 170 is adjacent to the bottom ring 154. By way of example, the rods 170 may be inserted through the rod openings 186 until the bottom collar 180 contacts a top surface 188 of the bottom ring 154. The bottom springs 182 may be placed over the lower end 182 of each of the rods 170 that extends through the rod openings 186 in the bottom ring 154. In one embodiment, the gears 175 may be coupled to the end of each of the rods 170 below the bottom springs 182. By way of example, the gears 175 may be slide fitted over the ends of the rods 170. Moreover, a glue (such as a slow-curing glue) may be applied to an inner surface of the gears 175 to facilitate bonding to the rods 170. However, while glue may be used, in certain embodiments, it may be desirable for the gears 175 to rotate with respect to the rods 170 until the desired phase angles of all gears 175 and the common driving gear (not shown) are set after mounting of the top ring 150, then glue may be applied. The top springs 172 may be placed over the threaded ends 176 of the rods 170. The threaded ends 176 of the rods 170 may be inserted the threaded rod openings 184 of the top ring 150. By way of example, the threaded ends 176 may be threaded into the threaded rod openings 184. While the threaded ends 176 are inserted through the threaded rod openings 184, the top ring 150 may be held parallel to the bottom ring 154. By way of example, the top ring 150 may be mounted in a position parallel to the bottom ring 154. An independent reference, such as two parallel plates, may be used to position the top ring 150 and the bottom ring 154 parallel with respect to one another. The gears 175 may be rotated to engage a driving gear (not shown). By way of example, the gears 175 may be rotated with respect to the rods 170 to engage the driving gear. Where glue is used, the glue placed on the inner surfaces of the gears 175 may set to lock the gears 175 and the rods 170, after the gears 175 have been engaged with the driving gear. Those of ordinary skill in the art will appreciate the present technique encompasses alternative methods of assembling the collimator assembly 12.

Figure 28:
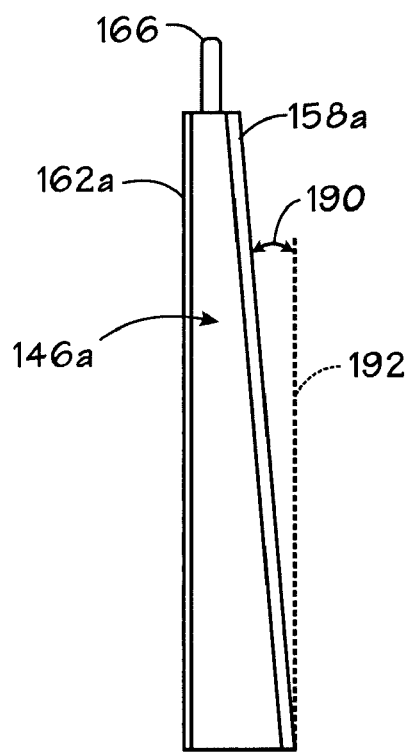
FIG. 28 is an illustration of one panel similar to the panels of the exemplary collimator assembly of FIG. 24 in accordance with embodiments of the present technique.

Referring now to FIG. 28, an exemplary panel 146a of the first set of panels 146 is illustrated, in accordance with an embodiment of the present technique. As previously described, the panel 146a includes a slit edge 158a and an interlocking side 162a. As illustrated, the slit edge 158a is angled with respect to the axial direction 192 of the panel 146a. Those of ordinary skill in the art will appreciate that this slit angle 190 may be varied to impact the adjustment of the aperture size of the adjustable slit aperture 108 defined the slit edge 158a and a corresponding slit edge (e.g., opposing slit edge 160a on FIG. 26) of one of the second set of panels 148. By way of example, reducing the slit angle 190 should increase the axial movement of the top ring 150 and/or the bottom ring 154 needed to adjust the aperture size. Similarly, increasing the slit angle 190 should decrease the axial movement needed to adjust the aperture size. Those of ordinary skill in the art should be able to select a suitable slit angle 190 based on a number of factors, included the desired resolution and sensitivity for a particular application. By way of example, a smaller slit angle 190 may be desired in higher resolution applications, while an increased slit angle 190 may be desired in lower resolution, higher sensitivity applications.

IV. Exemplary Combined Slit/Pinhole Aperture Collimator Embodiments

While specific reference is made in the present discussion to slit aperture collimators and pinhole aperture collimators, it should be appreciated that the present technique may be applicable to combined slit/pinhole aperture collimators. Combined slit/pinhole aperture collimators may be useful because the pinhole apertures may be focused on a small field of view while the slit apertures may be focused on a larger field of view that may, for example, overlap with the small field of view. By focusing the slit and pinhole apertures on different fields of view, activity outside the small field of view should be properly imaged and, thus, not be aliased into the small field of view during reconstruction. Also, the slit and pinhole apertures may provide complementary information about the distribution of a radiopharmaceutical tracer in various body tissues. By way of example, in a subject suspected of having cancer in a particular organ, the pinhole apertures could be focused on the target organ while the slit apertures could be focused on a large field of view in order to screen for metastatic tumors. Furthermore, the slit and pinhole apertures may have different spatial resolutions and sensitivities. By way of example, the image reconstruction quality may be improved by properly accounting for the combination of higher spatial resolution data over a small field of view and lower spatial resolution data over a larger field of view.

Figure 29:
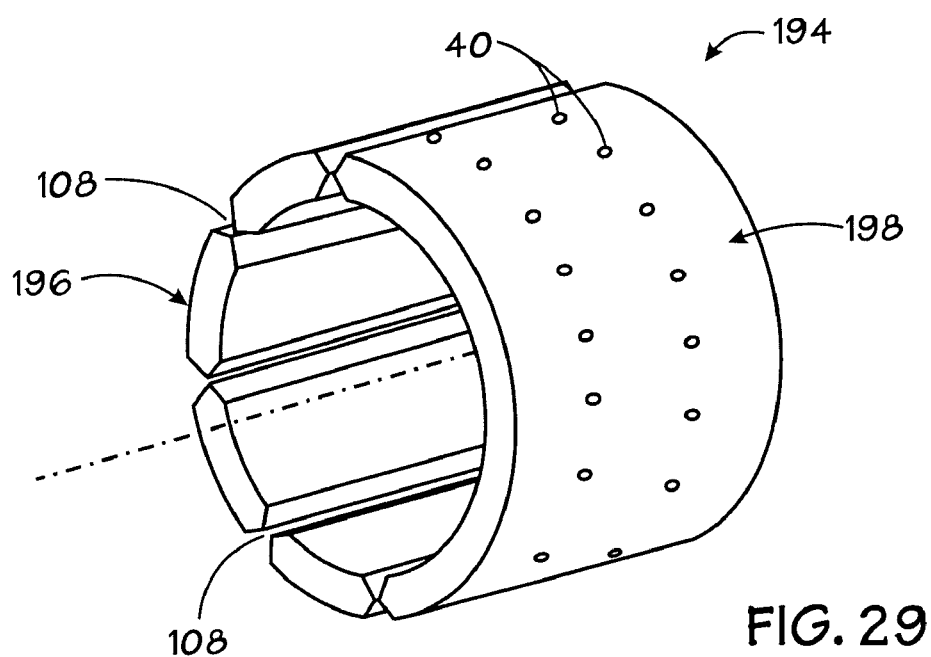
FIG. 29 is a perspective view an exemplary collimator assembly having a slit aperture portion and a pinhole aperture portion in accordance with embodiments of the present technique.

Referring now to FIG. 29, a combined collimator 194 is illustrated, in accordance with exemplary embodiments of the present technique. In the illustrated embodiment, the combined collimator 194 includes a slit aperture portion 196 having one or more adjustable slit apertures 108 therein and a pinhole aperture portion 198 having one or more adjustable pinhole apertures 40 therein. While not illustrated, the SPECT system 10 could further include one or more septa spaced on a side of the slit aperture portion 196 opposite from the field of view that would, for example, co-rotate with the combined collimator 194. At least one of the slit apertures 108 and/or at least one of the pinhole apertures 40 may have an aperture size that is adjustable. Any of the techniques described herein may be utilized for adjustment of the apertures size of the slit apertures and/or pinhole apertures with an adjustable aperture size. Moreover, the aperture size may be configured for adjustment during an examination.

While the preceding discussion has described the combined collimator 194 as having a single slit aperture portion 196 and a single pinhole aperture portion 198, one of ordinary skill in the art will recognize that the design may be extended to include multiple intermingled slit and pinhole aperture portions. In exemplary embodiments, for each slit aperture portion, a corresponding set of spaced septa could be placed between the combined collimator 194 and the detector assembly to define slit/septa gamma ray pathways. As will be appreciated, the combined collimator 194 may or may not rotate.

V. Exemplary Cross-Slit Aperture Collimator Embodiments

Figure 30:
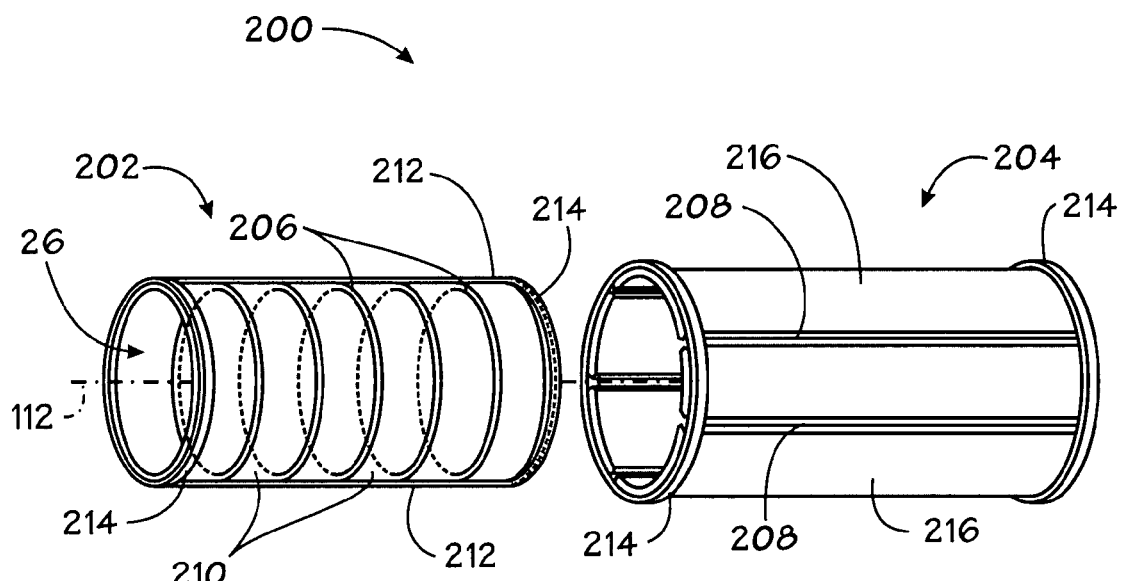
FIG. 30 is an exploded perspective view of an exemplary collimator assembly that includes an inner slit collimator and an outer slit collimator in accordance with embodiments of the present technique.

While specific reference in the preceding discussion is made to pinhole aperture collimators and slit aperture collimators with corresponding septa, it should be appreciated that the present technique is applicable to cross-slit aperture collimators. Referring now to FIG. 30, an exploded view of a cross-slit aperture collimator 200 is illustrated, which may be configured in accordance with exemplary embodiments of the present technique. In the illustrated embodiment, cross-slit aperture collimator 200 includes an inner slit aperture collimator 202 and an outer slit aperture collimator 204. As illustrated, the cross-slit aperture collimator 200 at least partially encloses the field of view 26. While FIG. 30 is an exploded view, the cross-slit aperture collimator 200 should be assembled so that the inner slit aperture collimator 202 is disposed closer to the field of view 26 than the outer slit aperture collimator 204. As will be discussed in more detail below, the cross-slit aperture collimator 200 should be configured such that the inner slits 206 in the inner slit aperture collimator 202 and the outer slits 208 in the outer slit aperture collimator 204 define one or more adjustable apertures through the cross-slit aperture collimator 200. Aperture size of least one of the inner slits 206 or the outer slits 208 may be adjusted to adjust the aperture size of the one or more adjustable apertures. Moreover, spacing between the inner surface(s) of the outer slit aperture collimator 204 and the outer surface(s) of the inner slit aperture collimator 202 may be chosen to position the outer slit aperture collimator 204 anywhere in the volume between the inner slit aperture collimator 202 and the detector assembly 14. By way of example, the outer slit aperture collimator 204 may be positioned close to but not touching the inner slit aperture collimator 202.

Further, the inner and outer slit collimators 202 and 204 may be mechanically coupled or placed in contact with each other, so as to rotate together, or they may be decoupled, so as to rotate separately as desired to adjust the positions of the apertures.

The inner slit aperture collimator 202 includes a plurality of inner slits 206 therein. In the illustrated embodiment, these inner slits 206 extend in a direction generally perpendicular to the longitudinal axis 112 of the cross-slit aperture collimator 200. In addition, the inner slit aperture collimator 202 includes a plurality of sections spaced along the longitudinal axis 112 such that spaces between the sections define the inner slits 206. By way of example, the spaced sections may include a plurality of inner cylindrical sections 210 spaced along the longitudinal axis 112 of the cross-slit aperture collimator 200 so as to define the inner slits 206. In the illustrated embodiments, the inner cylindrical sections 210 are coupled by rods 212 that extend in a direction parallel to the longitudinal axis 112. In exemplary embodiments, the rods 212 may be coupled to exterior surfaces of each of the inner cylindrical sections 210 of the inner slit aperture collimator 202. For further support, each end of the rods 212 may be coupled to a coupling mechanism, such as bands 214 or collars. By way of example, each of bands 214 may be coupled to the inner cylindrical sections 210 located at each end of the inner slit aperture collimator 202. While the inner cylindrical sections 210 of the inner slit aperture collimator 202 are illustrated as separate sections, the present technique encompasses the use of a unitary inner slit collimator. That is, the inner slit aperture collimator 202 may be fabricated as a solid piece having one or more slits therein. The inner slit aperture collimator 202 may also be constructed as a unitary piece in which the slits are filled by a material that provides mechanical support but that also allows most gamma rays to pass through the slit without interaction. Another example includes rods inserted though small holes drilled along the wall of cylindrical sections 210 (axial direction 112) and small spacers placed between cylindrical sections 210. The rods may run along the axial direction 112, for example.

The outer slit aperture collimator 204 includes a plurality of outer slits 208 therein. In the illustrated embodiment, the outer slits 208 extend in a direction generally parallel to the longitudinal axis 112 of the cross-slit aperture collimator 200. In addition, the outer slit aperture collimator 204 includes a plurality of sections spaced around the longitudinal axis 112 of the cross-slit aperture collimator 200 such that spaces between the sections define the outer slits 208. By way of example, the spaced sections may be or include a plurality of outer panels 216 spaced along and extending generally parallel to the longitudinal axis 112 of the cross-slit aperture collimator 200 so as to define the outer slits 208. For support, the outer panels 216 may be coupled by a coupling mechanism, such as bands 214 or collars. By way of example, each of the bands 214 may be coupled to each of the outer panels 216 at the respective ends of the cross-slit aperture collimator 200. While the outer panels 216 are illustrated in FIG. 30 as curved sections, the present technique encompasses the use of sections that are not curved. In addition, while the outer panels 216 are illustrated as separate sections, the present technique encompasses the use of a unitary outer slit collimator. That is, the outer slit aperture collimator 204 may be fabricated as a solid piece having one or more slits therein. The outer slit aperture collimator 204 may also be constructed as a unitary piece in which the slits are filled by a material that provides mechanical support but that also allows most gamma rays to pass through the slit without interaction.

Figure 31:
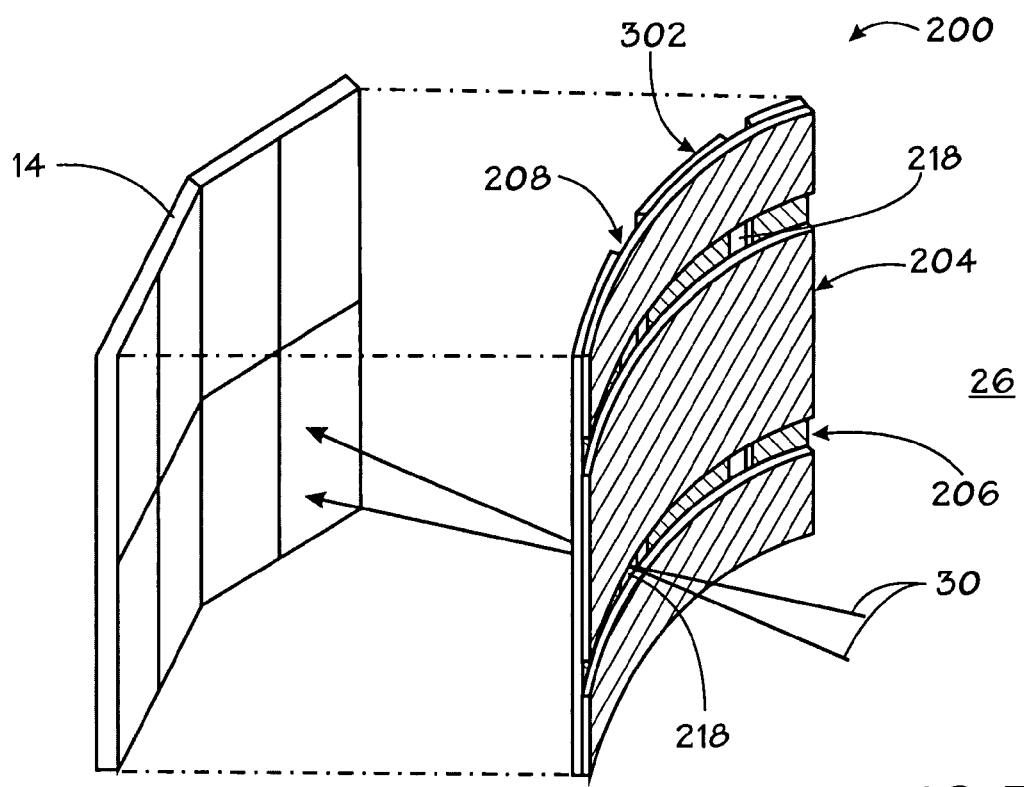
FIG. 31 is an illustration of a portion of a detector assembly and a portion of the collimator assembly of FIG. 30 in accordance with embodiments of the present technique.

Referring now to FIG. 31, a portion of the detector assembly 14 and a portion of the cross-slit aperture collimator 200 are illustrated to illustrate the apertures defined by the alignment of the inner slits 206 and the outer slits 208, in accordance with an embodiment of the present technique. As previously mentioned, the cross-slit aperture collimator 200 should be configured such that the inner slits 206 and the outer slits 208 define one or more adjustable apertures 218. Gamma rays 30 that do not pass through the one or more adjustable apertures 218 should be absorbed by the cross-slit aperture collimator 200. In the illustrated embodiment, the adjustable apertures are defined by the intersection of the inner slits 206 and the outer slits 208. The adjustable apertures 218 allow gamma rays 30 emanating from the field of view 26 to pass through the cross-slit aperture collimator 200 to impact the detector array 14.

Those of ordinary skill in the art will appreciate that the resolution of the SPECT system 10 is based in part on the aperture size of the one or more adjustable apertures 218. As previously mentioned, the adjustable apertures 218 have an aperture size that is adjustable. As the adjustable apertures 218 are defined by the intersection of the inner slits 206 and the outer slits 208, the size of the adjustable apertures 218 is based on the width of the inner slits 206 and the outer slits 208. In general, adjustment of the width of at least one of the inner slits 206 or the outer slits 208 should result in a corresponding aperture size adjustment for the adjustable apertures 218. In general, the inner slits 206 and/or the outer slits 208 may have the same or different widths. By way of example, the inner slits 206 and the outer slits 208 may have two or more different widths. In exemplary embodiments, each of the inner slits 206 and/or each of the outer slits 208 may have, or be adjusted, to a width in the range of from about 0.1 mm to about 10 mm, typically in the range of from about 1 mm to about 5 mm. Those of ordinary skill in the art will appreciate that the choice of slit widths depends upon the system geometry (e.g., detector array 14 location and subject field of view 26) and intended imaging applications. Adjustment of the adjustable apertures 218 to different sizes may provide different resolving power. By differing the aperture size, the spatial resolution and sensitivities of the SPECT system 10 may be changed. The image reconstruction algorithm should appropriately model the system response of the various apertures.

Moreover, in the illustrated embodiment, the inner slits 206 are generally orthogonal to the outer slits 208 (e.g., the angle of the intersection between the inner slits 206 and the outer slits 208 is approximately 90°). Because the slits are arranged in the orthogonal configuration, the adjustable apertures 218 defined by the cross-slit aperture collimator 200 forms a four-sided hole therethrough. As illustrated, the inner slits 206 and the outer slits 208 generally have the same width so that the adjustable apertures 218 defined by the intersection of the slits have a generally square shape. Exemplary embodiments of the present technique also may be provided with the inner slits 206 and the outer slits 208 having different widths so that the adjustable apertures 218 defined by the slits would have a generally rectangular shape. Moreover, exemplary embodiments of the present technique also may be provided with the inner slits 206 generally oblique to the outer slits 208 (e.g., the angle of the intersection between the inner slits 206 and the outer slits 208 is different from 90°), so that the adjustable apertures 218 defined by the intersection of the slits would have a generally rhombus or parallelogram shape. In addition, those of ordinary skill in the art will also appreciate that the spacing between the slits in the inner and outer slit aperture collimators 202 and 204 may or may not be constant throughout the cross-slit aperture collimator 200.

While the preceding discussion of FIGS. 30 and 31 has described the inner slit aperture collimator 202 as having inner slits 206 extending generally perpendicular to the longitudinal axis 112 of the cross-slit aperture collimator 200 and the outer slit aperture collimator 204 as having outer slits 208 extending in a direction generally parallel to the longitudinal axis 112, one of ordinary skill in the art will recognize that the present technique may be implemented with collimator assemblies having inner and outer slit aperture collimators 202 and 204 having alternative slit configurations. For example, the inner slits 206 may extend in a direction generally parallel to the longitudinal axis 112 of the cross-slit aperture collimator 200 while the outer slits 208 in outer slit aperture collimator 204 may extend in a direction generally perpendicular to the longitudinal axis 112 of the cross-slit aperture collimator 200. In another embodiment, the inner slits 206 and/or the outer slits 208 may extend in a direction generally diagonal to the longitudinal axis 112 of the cross-slit aperture collimator 200.

VI. Exemplary Combination SPECT/CT Embodiments

Figure 32:
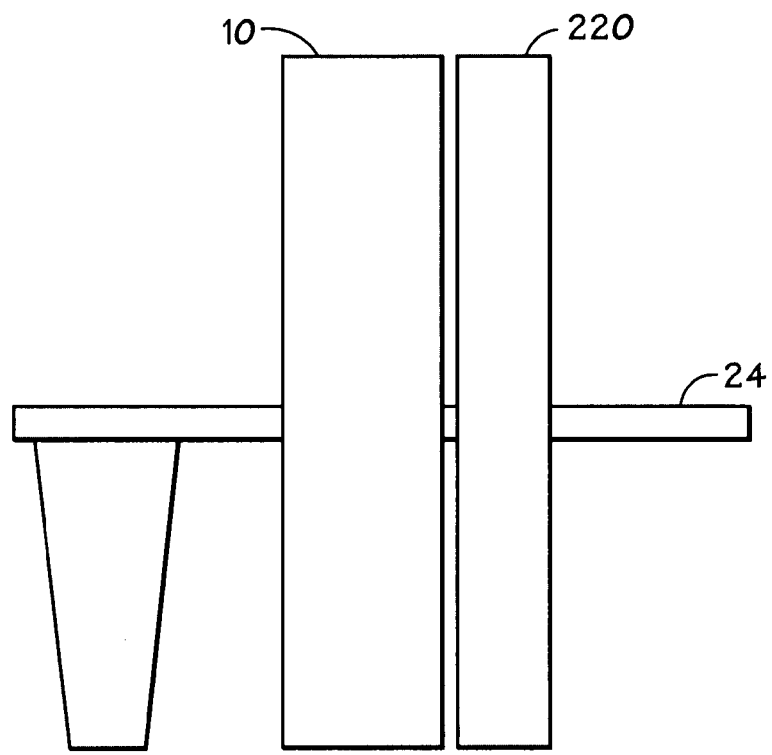
FIG. 32 is an illustration of an exemplary combined SPECT and computed tomography (CT) system in accordance with embodiments of the present technique.
Figure 33:
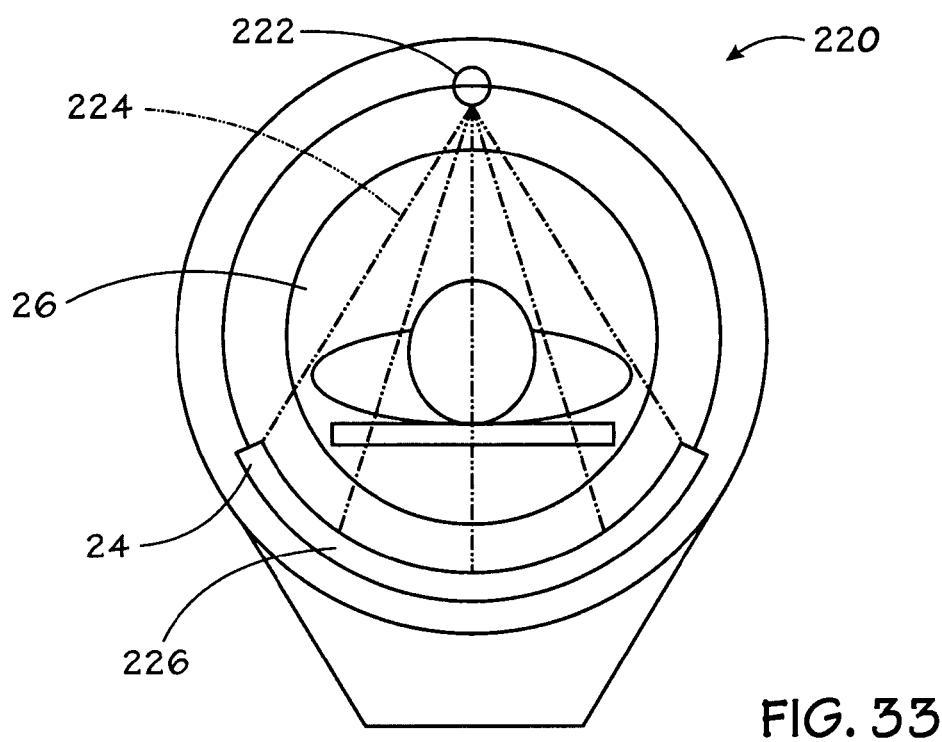
FIG. 33 is an illustration of an exemplary CT system that can be combined with a SPECT system, in accordance with embodiments of the present technique.

While specific reference in the present discussion is made to a SPECT system, it should be appreciated that the present technique is not intended to be limited to this or any other specific type of imaging system or modality. Rather, exemplary embodiments of the present technique may be used in conjunction with other imaging modalities, e.g., coded-aperture astronomy. In addition, SPECT system 10 may be combined with a second imaging system, such as a CT system or a magnetic resonance imaging (MRI) system. By way of example, the SPECT system 10 may be combined in the same gantry with a CT system. As illustrated in FIG. 32, a SPECT/CT imaging system includes SPECT system 10 and CT system 220. By way of example, the SPECT system 10 and the CT system 220 are shown as separate modules, aligned along a common longitudinal axis, and sharing a single subject support 24. As illustrated in FIG. 33, CT system 220 includes a source 222 of X-ray radiation configured to emit a stream of radiation 224 in the direction of the field of view 26 and an X-ray detector assembly 226 configured to generate one or more signals in response to the stream of radiation. Those of ordinary skill in the art will appreciate that in the third-generation CT configuration illustrated in FIG. 33, the source 222 and the X-ray detector assembly 226 generally rotate in synchrony around the field of view 26 while acquiring a plurality of lines of response passing through the subject, so that an X-ray tomographic attenuation image may be reconstructed. Other CT configurations may be employed, including the shared use of at least a portion of the SPECT detector assembly 14 as the X-ray detector assembly 226. Further, the SPECT and CT images may be acquired sequentially, in any order, by repositioning the subject, or concurrently by sharing the detector array. The images generated with the CT system 220 may then be used to generate gamma ray attenuation maps, for example, to calculate attenuation and/or scatter correction during the SPECT image reconstruction. In addition, the CT anatomical images may be combined with the SPECT functional images.

While the collimator assembly 12 is illustrated on the preceding figures as being generally cylindrically shaped, the present technique encompasses the employment of collimator assemblies that are not generally cylindrically shaped. By way of example, the collimator assembly 12 may be or include a flat panel having one or more adjustable apertures (e.g., adjustable pinhole apertures 40 or adjustable slit apertures 108) therein. Furthermore, one of ordinary skill in the art will recognize that the collimator assembly 12 and detector assembly 14 may be combined in modules and positioned to view portions of the field of view. If only a few collimator/detector modules are deployed, then they may be moved to a plurality of positions during image acquisition in order to acquire sufficient data for tomographic image reconstruction. Alternatively, if sufficient collimator/detector modules are deployed, then they may remain stationary during image acquisition and yet acquire sufficient data for tomographic image reconstruction.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A collimator assembly comprising:
a first set of panels spaced at least partially around a longitudinal axis of the collimator assembly and extending generally parallel to the longitudinal axis; and
a second set of panels spaced at least partially around the longitudinal axis of the collimator assembly and extending generally parallel to the longitudinal axis, said first set of panels and said second set of panels arranged in an alternating pattern, wherein the first set of panels and the second set of panels are arranged to define one or more slit apertures in the collimator assembly, wherein the collimator assembly is configured so that concurrent axial movement of at least one of the first set of panels or the second set of panels adjusts an aperture size of each of the one or more slit apertures, wherein gamma rays can pass though the one or more slit apertures, but the remainder of the collimator assembly is substantially gamma ray absorbent, and wherein the first set of panels are coupled to a top ring located at a first end of the collimator assembly and the second set of panels are coupled to a bottom ring located at a second end of the collimator assembly, wherein the first end is opposite the second end.

2. The collimator assembly of claim 1, wherein the collimator assembly comprises an inner collimator comprising the first set of panels and an outer collimator comprising the second set of panels, wherein the collimator assembly is configured so that rotation of at least one of the inner collimator or the outer collimator adjusts an aperture size of each of the one or more slit apertures.

3. The collimator assembly of claim 1, wherein each of the first set of panels comprises a first portion that overlaps with one of the second set of panels and a second portion, wherein a space between the second portion and another one of the second set of panels defines one of the one or more slit apertures.

4. The collimator assembly of claim 1, wherein the one or more slit apertures are defined by spaces between the first set of panels and the second set of panels.

5. The collimator assembly of claim 1, wherein a space between an edge of one of the first set of panels and an edge of one of the second set of panels defines one of the one or more slit apertures, wherein the collimator assembly is configured so that rotation of at least one of the edge of the first panel or the edge of the second panel adjusts an aperture size of the one of the one or more slit apertures.

6. The collimator assembly of claim 1, wherein each of the one or more slit apertures is defined by a space between an edge of one of the first set of panels and an edge of one of the second set of panels.

7. The collimator assembly of claim 6, wherein a side of each of the first set of panels opposite the slit edge of the respective panel of the first set is slidably interlocked with a different one of the second set of panels.

8. The collimator assembly of claim 1:

wherein the collimator assembly comprises first alignment pins, wherein each of the first set of panels is coupled to one of the first alignment pins at an end of the respective panel located at the second end of the collimator assembly, wherein each of the first alignment pins extends though a corresponding opening in the bottom ring; and wherein the collimator assembly comprises second alignment pins, wherein each of the second set of panels is coupled to one of the second alignment pins at an end of the respective panel located at the first end of the collimator assembly, wherein each of the second alignment pins extends though a corresponding opening in the top ring.

9. The collimator assembly of claim 1, wherein the collimator assembly comprises one or more rod assemblies disposed generally parallel to the longitudinal axis of the collimator assembly and configured to position at least one of the top ring or the bottom ring in an axial direction.

10. The collimator assembly of claim 9, where each of the one or more rod assemblies comprises a rod, wherein the rod comprises a threaded end disposed in a corresponding threaded opening in the top ring, and a lower end disposed though a corresponding rod opening in the lower ring.

11. The collimator assembly of claim 10, wherein each of the one or more rod assemblies comprises a top spring disposed over the rod between the top ring and an upper collar of the rod and a lower spring disposed over the lower end of the rod.

12. The collimator assembly of claim 11, wherein each of the one or more rod assemblies comprises a gear coupled to the lower end of the rod below the lower spring.

13. An imaging system comprising:

a collimator assembly comprising a first set of panels spaced around a longitudinal axis of the collimator assembly and extending generally parallel to the longitudinal axis, and a second set of panels spaced around the longitudinal axis of the collimator assembly and extending generally parallel to the longitudinal axis, said first set of panels and said second set of panels arranged in an alternating pattern, wherein the first set of panels and the second set of panels are arranged to define one or more slit apertures in the collimator assembly, and wherein the collimator assembly is configured so that concurrent axial movement of at least one of the first set of panels or the second set of panels adjusts an aperture size of each of the one or more slit apertures;

a detector assembly configured to generate one or more signals in response to gamma rays that pass though the one or more slit apertures in the collimator assembly, and wherein the first set of panels are coupled to a top ring located at a first end of the collimator assembly and the second set of panels are coupled to a bottom ring located at a second end of the collimator assembly, wherein the first end is opposite the second end.

14. The imaging system of claim 13, wherein the imaging system comprises a single photon emission computed tomography system or a combined single photon emission computed tomography system/x-ray computed tomography system.

15. The imaging system of claim 13, wherein the detector assembly comprises at least one of an array of solid-state detector elements or a scintillator assembly coupled to light sensors.

16. The imaging system of claim 13, comprising:

a module configured to receive the one or more signals and to process the one or more signals to generate one or more images; and an image display workstation configured to display the one or more images.

17. The imaging system of claim 13, wherein the collimator assembly comprises an inner collimator comprising the first set of panels and an outer collimator comprising the second set of panels, wherein the collimator assembly is configured so that rotation of at least one of the inner collimator or the outer collimator adjusts the aperture size of each of the one or more slit apertures.

18. The imaging system of claim 13, wherein a space between an edge of one of the first set of panels and an edge of one of the second set of panels defines one of the one or more slit apertures, wherein the collimator assembly is configured so that rotation of at least one of the edge of the first panel or the edge of the second panel adjusts the aperture size the one of the one or more slit apertures.

19. A method of adjusting collimator performance comprising:

moving axially at least one of a first set of panels of a collimator assembly or a second set of panels of the collimator assembly to concurrently adjust an aperture size of each slit aperture defined by the first set of panels and the second set of panels, said first set of panels and said second set of panels arranged in an alternating pattern, wherein the first set of panels are spaced at least partially around a longitudinal axis of the collimator assembly and extend generally parallel to the longitudinal axis, wherein the second set of panels are spaced at least partially around the longitudinal axis of the collimator assembly and extend generally parallel to the longitudinal axis, and wherein the first set of panels are coupled to a top ring located at a first end of the collimator assembly and the second set of panels are coupled to a bottom ring located at a second end of the collimator assembly, wherein the first end is opposite the second end;

collimating gamma rays with the collimator assembly; and detecting the collimated gamma rays.

20. The method of claim 19:

wherein the collimator assembly comprises an inner collimator comprising the first set of panels and an outer collimator comprising the second set of panels; and wherein moving at least one of the first set of panels or the second set of panels comprises rotating at least one of the inner collimator or the outer collimator.

21. The method of claim 20:

wherein a space between an edge of one of the first set of panels and an edge of one of the second set of panels defines one of the one or more slit apertures; and wherein moving at least one of the first set of panels or the second set of panels comprises rotating at least one of the edge of the first panel or the edge of the second panel.

* * * * *

UNITED STATES PATENT AND TRADEMARK OFFICE
CERTIFICATE OF CORRECTION

PATENT NO. : 7,723,690 B2
APPLICATION NO. : 11/731873
DATED : May 25, 2010
INVENTOR(S) : Uribe et al.

It is certified that error appears in the above-identified patent and that said Letters Patent is hereby corrected as shown below:

In the Specification:
In Fig. 22, Sheet 13 of 18, delete Tag "1142b" and insert Tag -- 142b --, therefor.

In Column 21, Line 29, delete "112" and insert -- 122 --, therefor.

In Column 21, Line 39, delete "1234" and insert -- 124 --, therefor.

In Column 28, Line 10, delete "though" and insert -- through --, therefor.

In the Claims:
In Column 31, Line 9, in Claim 1, delete "though" and insert -- through --, therefor.

In Column 31, Line 55, in Claim 8, delete "though" and insert -- through --, therefor.

In Column 31, Line 61, in Claim 8, delete "though" and insert -- through --, therefor.

In Column 32, Line 1, in Claim 10, delete "where" and insert -- wherein --, therefor.

In Column 32, Line 5, in Claim 10, delete "though" and insert -- through --, therefor.

In Column 32, Line 30, in Claim 13, delete "though" and insert -- through --, therefor.

In Column 32, Line 66, in Claim 18, after "size", insert -- of --.

Signed and Sealed this

Seventeenth Day of August, 2010

David J. Kappos
*Director of the United States Patent and Trademark Office*